(12) United States Patent
Hu et al.

(10) Patent No.: US 9,150,910 B2
(45) Date of Patent: Oct. 6, 2015

(54) METHODS AND COMPOSITIONS IN PARTICLE-BASED DETECTION OF TARGET MOLECULES USING LINKING MOLECULES

(75) Inventors: Celine Hu, Tiburon, CA (US); Jianping Xu, Pleasanton, CA (US); Hetian Gao, Fremont, CA (US); Julie Perkins, Sunnyvale, CA (US)

(73) Assignee: Headway Technologies, Inc., Milpitas, CA (US)

( * ) Notice: Subject to any disclaimer, the term of this patent is extended or adjusted under 35 U.S.C. 154(b) by 385 days.

(21) Appl. No.: 12/612,203

(22) Filed: Nov. 4, 2009

(65) Prior Publication Data

US 2010/0129819 A1    May 27, 2010

Related U.S. Application Data

(60) Provisional application No. 61/115,399, filed on Nov. 17, 2008.

(51) Int. Cl.
*C12Q 1/68* (2006.01)
*C07H 21/02* (2006.01)
*C07H 21/04* (2006.01)

(52) U.S. Cl.
CPC .................................. *C12Q 1/6834* (2013.01)

(58) Field of Classification Search
CPC ..... C12M 1/68; C12Q 1/6813; C12Q 1/6816; C12Q 1/6834; C12Q 1/68
USPC .................. 435/6.1; 536/23.1, 24.3
See application file for complete search history.

(56) References Cited

U.S. PATENT DOCUMENTS

| 4,599,303 | A | * | 7/1986 | Yabusaki et al. ............. 435/6.11 |
| 4,826,967 | A | | 5/1989 | Glass |
| 5,028,594 | A | | 7/1991 | Carson |
| 5,082,934 | A | | 1/1992 | Saba et al. |
| 5,124,246 | A | | 6/1992 | Urdea et al. |
| 5,196,306 | A | | 3/1993 | Bobrow et al. |
| 5,512,439 | A | | 4/1996 | Hornes et al. |
| 5,580,731 | A | | 12/1996 | Chang et al. |

(Continued)

FOREIGN PATENT DOCUMENTS

| JP | 2006-191932 A | 7/2006 |
| JP | 2007-189991 A | 8/2007 |

(Continued)

OTHER PUBLICATIONS

Wilson et al., A multiplexed PCR-coupled liquid bead array for the simultaneous detection of four biothreat agents. Molecular and Cellular Probes 19(2) : 137 (2005).*

(Continued)

*Primary Examiner* — Ethan C Whisenant
(74) *Attorney, Agent, or Firm* — Michael B. Rubin; Bozicevic, Field & Francis LLP

(57) ABSTRACT

Methods and compositions which can be used to increase the strength and/or probability of forming a binding complex comprising a target molecule and a substrate are disclosed. In one aspect, linking molecules are disclosed which can be used to increase the number of intra-complex binding interactions. Covalent bonds can be introduced to further increase the strength of these binding interactions. Inter-complex cross-linking can be utilized in connection with these methods to further strengthen and stabilize the disclosed binding complexes.

32 Claims, 20 Drawing Sheets

M (capture probe specific binding moiety)
N (capture probe)
A – C (target-specific binding moieties)

(56) References Cited

U.S. PATENT DOCUMENTS

| | | | |
|---|---|---|---|
| 5,616,464 A | | 4/1997 | Albagli et al. |
| 5,635,352 A | * | 6/1997 | Urdea et al. ................. 435/6.18 |
| 5,653,859 A | * | 8/1997 | Parton et al. .................. 204/450 |
| 5,767,259 A | | 6/1998 | Albagli et al. |
| 5,981,297 A | | 11/1999 | Baselt |
| 6,004,513 A | | 12/1999 | Albagli et al. |
| 6,005,093 A | | 12/1999 | Wood et al. |
| 6,177,243 B1 | | 1/2001 | Albagli et al. |
| 6,187,532 B1 | | 2/2001 | Wood et al. |
| 6,277,570 B1 | | 8/2001 | Wood et al. |
| 6,303,799 B1 | | 10/2001 | Cheng et al. |
| 6,495,676 B1 | | 12/2002 | Wood et al. |
| 6,573,048 B1 | | 6/2003 | Vanatta et al. |
| 6,590,091 B2 | | 7/2003 | Albagli et al. |
| 6,696,246 B1 | | 2/2004 | Huan et al. |
| 6,737,239 B2 | | 5/2004 | Wood et al. |
| 6,743,639 B1 | | 6/2004 | Tondra et al. |
| 6,800,768 B1 | | 10/2004 | Cheng et al. |
| 6,875,621 B2 | | 4/2005 | Tondra |
| 7,033,758 B2 | * | 4/2006 | Kenny et al. ................. 435/6.11 |
| 7,163,788 B2 | | 1/2007 | Tong et al. |
| 7,223,833 B1 | | 5/2007 | Nielsen et al. |
| 7,332,355 B2 | | 2/2008 | Hsieh-Wilson et al. |
| 2001/0012616 A1 | * | 8/2001 | Wood et al. ....................... 435/6 |
| 2002/0051971 A1 | | 5/2002 | Stuelpnagel et al. |
| 2002/0102578 A1 | | 8/2002 | Dickinson et al. |
| 2002/0127574 A1 | | 9/2002 | Mirkin et al. |
| 2002/0177157 A1 | | 11/2002 | Luo et al. |
| 2003/0148282 A1 | * | 8/2003 | Mirkin et al. ..................... 435/6 |
| 2003/0166177 A1 | | 9/2003 | Dordick et al. |
| 2005/0100930 A1 | | 5/2005 | Wang et al. |
| 2006/0177850 A1 | | 8/2006 | Schermer et al. |
| 2006/0252085 A1 | * | 11/2006 | Pollner et al. ..................... 435/6 |
| 2006/0286583 A1 | | 12/2006 | Luo et al. |
| 2007/0117151 A1 | | 5/2007 | Frederix et al. |
| 2007/0184436 A1 | | 8/2007 | Myerson et al. |
| 2007/0202576 A1 | | 8/2007 | Bodepudi et al. |
| 2008/0038725 A1 | * | 2/2008 | Luo et al. ........................ 435/6 |
| 2008/0220979 A1 | * | 9/2008 | Wang et al. ....................... 506/9 |
| 2009/0048123 A1 | | 2/2009 | Medintz et al. |
| 2009/0104707 A1 | | 4/2009 | Wang et al. |
| 2009/0111709 A1 | | 4/2009 | Burke et al. |
| 2010/0130383 A1 | | 5/2010 | Hu et al. |
| 2011/0059444 A1 | * | 3/2011 | Stromberg et al. ............... 435/6 |
| 2012/0289419 A1 | | 11/2012 | Hu et al. |

FOREIGN PATENT DOCUMENTS

| | | |
|---|---|---|
| WO | 90/11523 | 10/1990 |
| WO | 95/16055 A1 | 6/1995 |
| WO | 97/27317 A1 | 7/1997 |
| WO | 03/083440 A2 | 10/2003 |
| WO | WO03083440 | 10/2003 |
| WO | 2005/033343 A2 | 4/2005 |
| WO | 2006124711 | 11/2006 |
| WO | WO 2007005626 | 1/2007 |
| WO | 2007056250 | 5/2007 |
| WO | 2008/052775 | 5/2008 |
| WO | WO 2008101024 | 8/2008 |
| WO | WO 2009112498 | 9/2009 |

OTHER PUBLICATIONS

Graham et al., Magnetoresistive based biosensors and biochips. Trends in Biotechnology 22(9) :455 (Sep. 2004).Lai et al.*

Lai et al., Nucleic Acid-Based Cross-Linking Assay for Detection and Quantification of Hepatitis B Virus DNA. J. of Clinical Microbiology 37(1) :161 (1999).*

Mulvaney et al., Rapid, femtomolar bioassays in complex matrices combining microfluidics and magnetoelectronics. Biosensors & Bioelectronics 23 :191(Apr. 2007).*

Webb et al., Sequence-specific cross-linking of deoxyoligonucleotides via hybridization-triggered alkylation. JACS 108 : 2764 (1986).*

Shen et al., In situ detection of single micron-sized magnetic beads using magnetic tunnel junction sensors. Appl. Phys. Lett., 2005;86:253901(1-3).

Speel et al., Amplification methods to increase the sensitivity of in situ hybridization: Play Card(s). J. Hist. Cyt. 1999;47(3):281-8.

Spielmann et al., DNA structural reorganization upon conversion of a psoralen furan-side monoadduct to an interstrand cross-link: Implications for DNA repair. Proc. Natl. Acad. Sci. USA 1995;92:2345-9.

Sugino et al, Interaction of bacteriophage T4 RNA and DNA ligases in joining of duplex DNA at base-paired ends. J. Biol. Chem. 1977;252(11):3987-94.

Tornoe et al., Peptidotriazoles on solid phase: [1,2,3]-Triazoles by regiospecific copper(I)-catalyzed 1,3-dipolar cycloadditions of terminal alkynes to azides. J. Org. Chem. 2002;67:3057-64.

Van De Sande et al., T4 polynucleotide ligase catalyzed joining of short synthetic DNA duplexes at base-paired ends. Biochemistry 1978;17(4):723-9.

Wang et al., Towards a magnetic microarray for sensitive diagnostics. J. Magn. Magn. Mater. 2005;293:731-6.

Wang et al., Bioconjugation by copper(I)-catalyzed azide-alkyne [3+2] cycloaddition. J. Am. Chem. Soc. 2003;125: 3192-3.

Wittung et al., Interactions of DNA binding ligands with PNA-DNA hybrids. Nucleic Acids Research 1994;22(24):5371-7.

Wu et al., Efficiency and fidelity in a click-chemistry route to triazole dendrimers by the copper(I)-catalyzed ligation of azides and alkynes. Angrew. Chem. Int. Ed. 2004;43:3928-32.

Yoo et al., Copper-catalyzed synthesis of N-sulfonyl-1,2,3-triazoles: Controlling selectivity. Angew. Chem. Int. Ed. 2007;46:1730-3.

Baselt et al., A biosensor based on magnetoresistance technology. Biosens. Bioelectron. 1998;13(7-8):731-9.

Baskin et al., Copper-free click chemistry for dynamic in vivo imaging. Proc. Natl. Acad. Sci. USA 2007;104(43):16793-7.

Bird et al., Single-chain antigen-binding proteins. Science 1988;242:423-6.

Casey, 2005 Nobel Prize in Chemistry: Development of the olefin metathesis method in organic synthesis. J. Chem. Edu. 2006;83(2):192-5.

Chan et al., Polytriazoles as copper(I)-stabilizing ligands in catalysis. Org. Lett. 2004;6(17):2853-5.

Chavali et al., Oligonucleotide properties determination and primer designing: a critical examination of predictions. Bioinformatics 2005;21(20):3918-25.

Donnelly et al., 'Click' cycloaddition catalysts: copper(I) and copper(II) tris(triazolylmethyl)amine complexes. Chem. Commun. 2008:2459-61.

Drake et al., Gd-doped iron-oxide nanoparticles for tumour therapy via magnetic field hyperthermia. J. Mater. Chem. 2007;17:4914-8.

Ebright et al., Conversion of a helix-turn-helix motif sequence-specific DNA binding protein into a site-specfic DNA cleavage agent. Proc. Natl. Acad. Sci. USA 1990;87:2882-6.

Edelstein et al., The BARC biosensor applied to the detection of biological warfare agents. Biosens. Bioelectron. 2000;14:pp. 805-813.

Ferreira et al., Biodetection using magnetically labeled biomolecules and arrays of spin valve sensors (invited). J. Appl. Phys. 2003;93(10):7281-6.

Ferreira et al., Effect of spin-valve sensor magnetostatic fields on nanobead detection for biochip applications. J Appl. Phys. 2005;97(10Q904):1-3.

Graham et al., Single magnetic microsphere placement and detection on-chip using current line designs with integrated spin valve sensors: Biotechnological applications. J. Appl. Phys. 2002;91(10):7786-8.

He et al., Empirical establishment of oligonucleotide probe design criteria. Appl. Env. Microbiol. 2005;71(7):3753-60.

Himo et al., Copper(I)-catalyzed synthesis of azoles. DFT study predicts unprecedented reactivity with intermediates. J. Amer. Chem. Soc. 2005;127:210-6.

Hunkapiller et al., The growing immunoglobulin gene superfamily. Nature 1986;323:15-6.

Huston et al., Protein engineering of antibody binding sites: Recovery of specific activity in an anti-digoxin single-chain Fv analogue produced in *Escherichia coli*. Proc. Natl. Acad. Sci. USA 1988;85:5879-83.

(56) References Cited

OTHER PUBLICATIONS

IBM Almaden Research Center, Magnetic Tunnel Junctions (MTJs).
Ito et al., Development of an artificial antibody system with multiple valency using an Fv fragment fused to a fragment of protein A. J. Biol. Chem. 1993;268(27):20668-75.
Kim et al., Site-specific gene modification by PNAs conjugated to psoralen. Biochemistry 2006;45:314-23.
Kocalka et al., Rapid and efficient DNA strand cross-linking by click chemistry. Chembiochem 2008;9:1280-5.
Kolb et al., The growing impact of click chemistry on drug discovery. Drug Discovery Today 2003;8(24):1128-37.
Krasia et al., Formation of oligotriazoles catalysed by cucurbituril. Chem. Commun. 2002:22-23.
Lanzavecchia et al., The use of hybrid hybridomas to target human cytotoxic T lymphocytes. Eur. J. Immunol. 1987;17:105-11.
Lewis et al., Discovery and characterization of catalysts for azide-alkyne cycloaddition by fluorescence quenching. J. Am. Chem. Soc. 2004;126:9152-3.
Li et al., Detection of single micron-sized magnetic bead and magnetic nanoparticles using spin valve sensors for biological applications. J. Appl. Phys. 2003;93(10):7557-9.
Li et al., Model and experiment of detecting multiple magnetic nanoparticles as biomolecular labels by spin valve sensors. IEEE Trans. Magn., 2004;40:3000-2.
Li et al., Selection of optimal oligonucleotide probes for microarrays using multiple criteria, global alignment and parameter estimation. Nucleic Acids Research 2005;33(19):6114-23.
Lin et al., Mechanistic investigation of the Staudinger ligation. J. Am. Chem. Soc. 2005;127:2686-95.
Long et al., Localized "click" chemistry through dip-pen nanolithography. Adv. Mat. 2007;19:4471-3.
Luo et al., Controlled assembly of dendrimer-like DNA. Nature Materials 2004;3:38-42.
Lynn et al., Water-soluble ruthenium alkylidenes: Synthesis, characterization, and application to olefin metathesis in protic solvents. J. Am. Chem. Soc. 2000;122: 6601-9.
Miller et al., A DNA array sensor utilizing magnetic microbeads and magnetoelectronic detection. J. Magn. Magn. Mater., 2001;225:138-44.
Mottes et al., Restoration by T4 ligase of DNA sequences sensitive to "flush"-cleaving restriction enzyme. Nucleic Acids Research 1977;4(7):2467-76.
Nagasaki et al., Photoenhancement of transfection efficiency using novel cationic lipids having a photocleavable spacer. Bioconjugate Chem. 2003;14:513-6.
Okamoto et al., Synthesis and properties of peptide nucleic acids containing a psoralen unit. Org. Lett. 2001;3(6):925-7.
Pendergrast et al., Determination of the orientation of a DNA binding motif in a protein-DNA complex by photocrosslinking. Proc. Nati. Acad. Sci. USA 1992;89:10287-91.
Praseuth et al., Double helices with parallel strands are formed by nuclease-resistant oligo-[α]-deoxynucleotides and oligo-[α]-deoxynucleotides covalently linked to an intercalating agent with complementary oligo-[β]-deoxynucleotides. J. Mol. Biol. 1987;196:939-42.
Praseuth et al., Sequence-specific binding and photocrosslinking of α and β oligodeoxynucleotides to the major groove of DNA via triple-helix formation. Proc. Natl. Acad. Sci. USA 1988;85:1349-53.
Rodionov et al., Mechanism of the ligand-free Cu(I)-catalyzed azide-alkyne cycloaddition reaction. Angrew. Chem. Int. Ed. 2005;44:2210-5.
Rostovtsev et al., A stepqise Huisgen cycloaddition process: Copper(I)-catalyzed regioselective "ligation" of azides and terminal alkynes. Angew. Chem. Int. Ed. 2002;41(14):2596-9.
Ruparel et al., Design and synthesis of a 3'-O-allyl photocleavable fluorescent nucleotide as a reversible terminator for DNA sequencing by synthesis. Proc. Natl. Acad. Sci. 2006;102(17):5932-7.
Saffran et al., Preparation and characterization of biotinylated psoralen. Nucleic Acids Research 1988;16(15):7221-31.
Salic et al., A chemical method for fast and sensitive detection of DNA synthesis in vivo. Proc. Natl. Acad. Sci. 2008;105(7):2415-20.
Saravis et al., Amplified immunoperoxidase staining of isoelectrically focused human tumor markers. Elecrophoresis 1980;1:191-3.
Saxon et al., Cell surface engineering by a modified Staudinger reaction. Science 2000;287(5460):2007-10.
Schrag et al., Magnetic tunnel junction sensor development for industrial applications. Micro Magnetics, Inc.
Seol et al., Gold nanoparticles: enhanced optical trapping and sensitivity coupled with significant heating. Optics Letters 2006;31(16):2429-31.
Shchepinov et al., Oligonucleotide dendrimers: synthesis and sue as polylabelled DNA probes. Nucleic Acids Research 1997;25(22):4447-54.
Shchepinov et al., Oligonucleotide dendrimers: stable nano-structures. Nucleic Acids Research 1999;27(15):3035-41.
Collins, et al., A branched DNA signal amplification assay for quantification of nucleic acid targets below 100 molecules/ml., Nucleic Acids Res. Aug. 1, 1997; 25(15): 2979-2984.
Gramlich et al. (2008) "Postsynthetic DNA Modification through the Copper-Catalyzed Azide-Alkyne Cycloaddition Reaction" *Angew Chem Int Ed* 47:8350-8358.
Park, et al. (2002) "Array-Based Electrical Detection of DNA with Nanoparticle Probes" *Science* 295(5559):1503-1506.
Joshi et al. (2004) "A Three-Component Mannich Type Reaction for Selective Tyrosine Bioconjugation" J Am Chem Soc 126(49):15942-15943.
Martins et al. (2009) "Femtomolar Limit of Detection with a Magnetoresistive Biochip" Biosens Bioelectron 24(8):2690-2695.
Gryaznov & Letsinger (1993) "Chemical Ligation of Oligonucleotides in the Presence and Absence of a Template" 115:3808-3809.
Molecular Probes: Invitrogen Detection Technologies "Invitrogen Tyramide Signal Amplification Kit" Dec. 5, 2005, pp. 1-6.
Invitrogen by Life Technologies; "Dynabeads® M-280 Streptavidin"; Catalog Nos. 11205D, 11206D, 60210: Oct. 2011; 2 pages.

\* cited by examiner

M (capture probe specific binding moiety)
N (capture probe)
A – D (target-specific binding moieties)

M (capture probe specific binding moiety)
N (capture probe)
A – G (target-specific binding moieties)

Target Molecule

M (capture probe specific binding moiety)
N (capture probe)
A – G (target-specific binding moieties)

Target Molecule

M (capture probe specific binding moiety)
N (capture probe)
A (target-specific binding moiety)

M (capture probe specific binding moiety)
N (capture probe)
A – C (target-specific binding moieties)

M (capture probe specific binding moiety)
N (capture probe)
A – C (target-specific binding moieties)

C1, C2 (Capture probes)

L1, L2 (Linking molecules)

Substrate 2
Biochip surface

METHODS AND COMPOSITIONS IN PARTICLE-BASED DETECTION OF TARGET MOLECULES USING LINKING MOLECULES

CROSS REFERENCE TO RELATED APPLICATION

This application claims priority to U.S. Provisional Patent Application No. 61/115,399 filed Nov. 17, 2008, which is incorporated herein by reference in its entirety and for all purposes.

BACKGROUND

Magnetic sensing capabilities developed in electronics and semiconductor industries in applications such as the read heads in hard drives have seen great advancements in the last couple decades with higher sensitivity and density. In recent years there has been much interest in applying these capabilities to the detection of biomolecules. The present disclosure addresses these issues, and provides related advantages.

SUMMARY OF THE INVENTION

Methods and compositions which can be used to increase the strength and/or probability of forming a binding complex comprising a nucleic acid target molecule and a substrate are disclosed. In one aspect, linking molecules are disclosed which can be used to increase the number of intra-complex binding interactions in a complex comprising a nucleic acid target molecule and a substrate. Covalent bonds can be introduced to further increase the strength of these binding interactions. Inter-complex cross-linking can be utilized in connection with these methods to further strengthen and stabilize the disclosed binding complexes.

In a first aspect, the present disclosure provides a method of generating a complex comprising a nucleic acid target molecule, wherein the method comprises: combining in a reaction mixture a substrate, wherein the substrate comprises a plurality of capture probes bound thereto; a sample suspected of containing a nucleic acid target molecule; and a linking molecule. The linking molecule in turn comprises one or more target-specific binding moieties which specifically bind to the nucleic acid target molecule, when present. When the linking molecule comprises multiple target-specific binding moieties, each of the target-specific binding moieties specifically binds to a different region of the nucleic acid target molecule when present. The linking molecule also comprises one or more capture probe-specific binding moieties which specifically bind to at least one of the plurality of capture probes bound to the substrate surface. When the linking molecule comprises a single target-specific binding moiety, the linking molecule comprises a plurality of capture probe-specific binding moieties, and when the linking molecule comprises a single capture probe-specific binding moiety, the linking molecule comprises a plurality of target-specific binding moieties. The method further requires that the combining is under reaction conditions sufficient to provide for specific binding of the linking molecule to the nucleic acid target molecule, if present, and to at least one of the plurality of capture probes. The methods optionally includes, adding to the reaction mixture a cross-linking agent to form covalent bonds between specifically bound nucleic acid molecules, if present. When the nucleic acid target molecule is present in the sample, the linking molecule specifically binds to the nucleic acid target molecule and one or more of the capture probes bound to the substrate, thereby forming a complex comprising the nucleic acid target molecule, the linking molecule and the substrate.

The method can further comprise detecting the presence or absence of the complex.

In one embodiment, the method results in formation of the complex.

In another embodiment, the method further comprises cross-linking at least two members of the complex.

In another embodiment of the method, the linking molecule comprises a plurality of the target-specific binding moieties and one of the capture probe-specific binding moieties.

In another embodiment of the method, the linking molecule comprises one of the target-specific binding moieties and a plurality of the capture probe-specific binding moieties.

In another embodiment of the method, the linking molecule comprises a plurality of the target-specific binding moieties and a plurality of the capture probe-specific binding moieties.

In one embodiment of the method, a plurality of complexes is formed, wherein each member of the plurality comprises a nucleic acid target molecule, a linking molecule and a substrate. In one such embodiment, the method further comprises adding to the reaction mixture a cross-linking agent to link at least two of the plurality of complexes via one or more covalent bonds.

In one embodiment of the method, the substrate comprises a biochip surface. In another embodiment of the method, the substrate is a detectable label. In one embodiment where the substrate is a detectable label, the detectable label is a magnetic particle.

In a second aspect of the present disclosure, an embodiment of the method described in the first aspect is disclosed, wherein the substrate is a detectable label, and wherein the method further comprises including in the reaction mixture a substrate comprising a biochip surface, wherein the biochip surface comprises at least one target-immobilization probe bound thereto, and wherein the combining is under reaction conditions sufficient to provide for specific binding of the nucleic acid target molecule, if present, to the target-immobilization probe. When the nucleic acid target molecule is present in the sample, the target-immobilization probe specifically binds to the nucleic acid target molecule, the nucleic acid target molecule specifically binds to the linking molecule and the linking molecule specifically binds to one or more of the capture probes bound to the detectable label, thereby forming a complex comprising the biochip surface, the target-immobilization probe, the nucleic acid target molecule, the linking molecule and the detectable label.

In one embodiment of the method described in the second aspect of the present disclosure, the method further comprises detecting the presence or absence of the complex comprising the biochip surface, the target-immobilization probe, the nucleic acid target molecule, the linking molecule and the detectable label.

In another embodiment of the method described in the second aspect of the present disclosure, the method results in formation of the complex comprising the biochip surface, the target-immobilization probe, the nucleic acid target molecule, the linking molecule and the detectable label. In one such embodiment, the method further comprises cross-linking at least two members of the complex comprising the biochip surface, the target-immobilization probe, the nucleic acid target molecule, the linking molecule and the detectable label.

In another embodiment of the method described in the second aspect of the present disclosure, the linking molecule comprises a plurality of the target-specific binding moieties and one of the capture probe-specific binding moieties.

In another embodiment of the method described in the second aspect of the present disclosure, the linking molecule comprises one of the target-specific binding moieties and a plurality of the capture probe-specific binding moieties.

In another embodiment of the method described in the second aspect of the present disclosure, the linking molecule comprises a plurality of the target-specific binding moieties and a plurality of the capture probe-specific binding moieties.

In another embodiment of the method described in the second aspect of the present disclosure, the complex comprising the biochip surface, the target-immobilization probe, the nucleic acid target molecule, the linking molecule and the detectable label does not comprise more than one detectable label.

In another embodiment of the method described in the second aspect of the present disclosure, the complex comprising the biochip surface, the target-immobilization probe, the nucleic acid target molecule, the linking molecule and the detectable label does not comprise more than one target molecule.

In another embodiment of the method described in the second aspect of the present disclosure, a plurality of complexes are formed, wherein each member of the plurality comprises a biochip surface, a target-immobilization probe, a nucleic acid target molecule and a detectable label, and the method further comprises adding to the reaction mixture a cross-linking agent to link at least two of the plurality of complexes via one or more covalent bonds.

In another embodiment of the method described in the second aspect of the present disclosure, the detectable label is a magnetic particle.

In a third aspect of the present disclosure, an embodiment of the method described in the first aspect is disclosed, wherein the substrate is a detectable label, and wherein the method further comprises including in the reaction mixture a substrate comprising a biochip surface, wherein the biochip surface comprises a plurality of capture probes bound thereto. The method also further comprises including in the reaction mixture a second linking molecule, wherein the second linking molecule comprises one or more target-specific binding moieties which specifically bind to the nucleic acid target molecule, when present. When the second linking molecule comprises multiple target-specific binding moieties, each of the target-specific binding moieties specifically binds to a different region of the nucleic acid target molecule when present. The second linking molecule also comprises one or more capture probe-specific binding moieties which specifically bind to at least one of the plurality of capture probes bound to the biochip surface. When the second linking molecule comprises a single target-specific binding moiety, the second linking molecule comprises a plurality of capture probe-specific binding moieties, and when the second linking molecule comprises a single capture probe-specific binding moiety, the second linking molecule comprises a plurality of target-specific binding moieties. The combining is under reaction conditions sufficient to provide for specific binding of the second linking molecule to the nucleic acid target molecule, if present, and to at least one of the plurality of capture probes bound to the biochip surface. When the nucleic acid target molecule is present in the sample, the linking molecule specifically binds to the nucleic acid target molecule and one or more of the capture probes bound to the detectable label, and the second linking molecule specifically binds to the nucleic acid target molecule and one or more of the capture probes bound to the biochip surface, thereby forming a complex comprising the detectable label, the linking molecule, the nucleic acid target molecule, the second linking molecule and the biochip surface.

In one embodiment of the method described in the third aspect of the present disclosure, the method further comprises detecting the presence or absence of the complex comprising the detectable label, the linking molecule, the nucleic acid target molecule, the second linking molecule and the biochip surface.

In another embodiment of the method described in the third aspect of the present disclosure, the method results in formation of the complex comprising the detectable label, the linking molecule, the nucleic acid target molecule, the second linking molecule and the biochip surface. In one such embodiment, the method further comprises cross-linking at least two members of the complex comprising the detectable label, the linking molecule, the nucleic acid target molecule, the second linking molecule and the biochip surface.

In another embodiment of the method described in the third aspect of the present disclosure, the second linking molecule comprises a plurality of the target-specific binding moieties and one of the capture probe-specific binding moieties.

In another embodiment of the method described in the third aspect of the present disclosure, the second linking molecule comprises one of the target-specific binding moieties and a plurality of the capture probe-specific binding moieties.

In another embodiment of the method described in the third aspect of the present disclosure, the second linking molecule comprises a plurality of the target-specific binding moieties and a plurality of the capture probe-specific binding moieties.

In another embodiment of the method described in the third aspect of the present disclosure, the complex comprising the detectable label, the linking molecule, the nucleic acid target molecule, the second linking molecule and the biochip surface does not comprise more than one detectable label.

In another embodiment of the method described in the third aspect of the present disclosure, the complex comprising the detectable label, the linking molecule, the nucleic acid target molecule, the second linking molecule and the biochip surface does not comprise more than one target molecule.

In another embodiment of the method described in the third aspect of the present disclosure, a plurality of complexes are formed, wherein each member of the plurality comprises a biochip surface, first and second linking molecules, a nucleic acid target molecule, and a detectable label, and the method further comprises adding to the reaction mixture a cross-linking agent to link at least two of the plurality of complexes via one or more covalent bonds.

In one embodiment of the method described in the third aspect of the present disclosure, the detectable label is a magnetic particle.

In a fourth aspect, the present disclosure provides a method of generating a complex comprising a nucleic acid target molecule, said method comprising combining in a reaction mixture a substrate, wherein said substrate comprises a plurality of capture probe bound thereto; a sample suspected of containing a nucleic acid target molecule; and a plurality of linking molecules. Each member of the plurality of linking molecules is independently present in one or more copies, and each member comprises a target-specific binding moiety which specifically binds to a different region of the nucleic acid target molecule, when present. Each member of the plurality of linking molecules also comprises a capture probe-specific binding moiety which specifically binds to a capture probe of the plurality of capture probes. The combining is under reaction conditions sufficient to provide for specific binding of the plurality of linking molecules to the nucleic acid target molecule, if present, and to a plurality of the capture probes bound to the substrate. The method optionally includes adding to the reaction mixture a cross-linking agent to form covalent bonds between specifically bound nucleic acid molecules, if present. When the nucleic acid target molecule is present in the sample, the plurality of linking molecules specifically binds to a plurality of different regions of the nucleic acid target molecule and a plurality of the capture probes bound to the substrate, thereby forming a complex comprising the nucleic acid target molecule, the plurality of linking molecules, and the substrate.

In one embodiment of the method described in the fourth aspect of the present disclosure, the method further comprises detecting the presence or absence of the complex.

In another embodiment of the method described in the fourth aspect of the present disclosure, the method results in formation of the complex. In one such embodiment, the method further comprises cross-linking at least two members of the complex.

In another embodiment of the method described in the fourth aspect of the present disclosure, a plurality of complexes are formed, wherein each member of the plurality comprises a biochip surface, a plurality of linking molecules, a nucleic acid target molecule, and a detectable label, and the method further comprises adding to the reaction mixture a cross-linking agent to link at least two of the plurality of complexes via one or more covalent bonds.

In one embodiment of the method described in the fourth aspect of the present disclosure, the substrate comprises a biochip surface. In another embodiment, the substrate is a detectable label. In one embodiment where the substrate is a detectable label, the detectable label is a magnetic particle.

In a fifth aspect, the present disclosure provides a method as described in the fourth aspect of the present disclosure, wherein the substrate is a detectable label, and wherein the method further comprises including in the reaction mixture a substrate comprising a biochip surface, wherein the biochip surface comprises at least one target-immobilization probe bound thereto, and wherein the combining is under reaction conditions sufficient to provide for specific binding of the nucleic acid target molecule, if present, to the target-immobilization probe. When the nucleic acid target molecule is present in the sample, the target-immobilization probe specifically binds to the nucleic acid target molecule, the nucleic acid target molecule specifically binds to the plurality of linking molecules and the plurality of linking molecules specifically binds to a plurality of the capture probes bound to the detectable label, thereby forming a complex comprising the biochip surface, the target-immobilization probe, the nucleic acid target molecule, the plurality of linking molecules and the detectable label.

In one embodiment of the method described in the fifth aspect of the present disclosure, the method further comprises detecting the presence or absence of the complex comprising the biochip surface, the target-immobilization probe, the nucleic acid target molecule, the plurality of linking molecules and the detectable label.

In another embodiment of the method described in the fifth aspect of the present disclosure, the method results in formation of the complex comprising the biochip surface, the target-immobilization probe, the nucleic acid target molecule, the plurality of linking molecules and the detectable label. In one such embodiment, the method further comprises cross-linking at least two members of the complex comprising the biochip surface, the target-immobilization probe, the nucleic acid target molecule, the plurality of linking molecules and the detectable label.

In another embodiment of the method described in the fifth aspect of the present disclosure, the complex comprising the biochip surface, the target-immobilization probe, the nucleic acid target molecule, the plurality of linking molecules and the detectable label does not comprise more than one detectable label.

In another embodiment of the method described in the fifth aspect of the present disclosure, the complex comprising the biochip surface, the target-immobilization probe, the nucleic acid target molecule, the plurality of linking molecules and the detectable label does not comprise more than one target molecule.

In another embodiment of the method described in the fifth aspect of the present disclosure, a plurality of complexes are formed, each member of the plurality comprising a biochip surface, a target-immobilization probe, a nucleic acid target molecule, a plurality of linking molecules and a detectable label, and the method further comprises adding to the reaction mixture a cross-linking agent to link at least two of the plurality of complexes via one or more covalent bonds.

In one embodiment of the method described in the fifth aspect of the present disclosure, the detectable label is a magnetic particle.

In a sixth aspect, the present disclosure provides a method as described in the fourth aspect of the present disclosure, wherein the substrate is a detectable label, and wherein the method further comprises including in the reaction mixture a substrate comprising a biochip surface, wherein the biochip surface comprises a plurality of capture probes bound thereto. The method also further comprises including in the reaction mixture a second plurality of linking molecules, wherein each member of the second plurality of linking molecules is independently present in one or more copies. Each member of the second plurality of linking molecules comprises a target-specific binding moiety which specifically binds to a different region of the nucleic acid target molecule, when present. Each member of the second plurality of linking molecules also comprises a capture probe-specific binding moiety which specifically binds to a capture probe of the plurality of capture probes bound to the biochip surface. The combining is under reaction conditions sufficient to provide for specific binding of the second plurality of linking molecules to the nucleic acid target molecule, if present, and to a plurality of the capture probes bound to the biochip surface. When the nucleic acid target molecule is present in the sample, the plurality of linking molecules specifically binds to the nucleic acid target molecule and a plurality of the capture probes bound to the detectable label, and the second plurality of linking molecules specifically binds to the nucleic acid target molecule and a plurality of the capture probes bound to the biochip surface, thereby forming a complex comprising the detectable label, the plurality of linking molecules, the nucleic acid target molecule, the second plurality of linking molecules and the biochip surface.

In one embodiment of the method described in the sixth aspect of the present disclosure, the method further comprises detecting the presence or absence of the complex comprising the detectable label, the plurality of linking molecules, the nucleic acid target molecule, the second plurality of linking molecules and the biochip surface.

In another embodiment of the method described in the sixth aspect of the present disclosure, the method results in formation of the complex comprising the detectable label, the plurality of linking molecules, the nucleic acid target molecule, the second plurality of linking molecules and the biochip surface. In one such embodiment, the method further comprises cross-linking at least two members of the complex comprising the detectable label, the plurality of linking molecules, the nucleic acid target molecule, the second plurality of linking molecules and the biochip surface.

In another embodiment of the method described in the sixth aspect of the present disclosure, the complex comprising the detectable label, the plurality of linking molecules, the nucleic acid target molecule, the second plurality of linking molecules and the biochip surface does not comprise more than one detectable label.

In another embodiment of the method described in the sixth aspect of the present disclosure, the complex comprising the detectable label, the plurality of linking molecules, the nucleic acid target molecule, the second plurality of linking molecules and the biochip surface does not comprise more than one target molecule.

In another embodiment of the method described in the sixth aspect of the present disclosure, a plurality of complexes is formed, wherein each member of the plurality comprises a detectable label, a plurality of linking molecules, a nucleic acid target molecule, a second plurality of linking molecules and a biochip surface, and the method further comprises adding to the reaction mixture a cross-linking agent to link at least two of the plurality of complexes via one or more covalent bonds.

In one embodiment of the method described in the sixth aspect of the present disclosure, the detectable label is a magnetic particle.

In a seventh aspect, the present disclosure provides a reaction mixture comprising a substrate, wherein the substrate comprises a plurality of capture probes bound thereto; a sample suspected of containing a nucleic acid target molecule; and a linking molecule. The linking molecule comprises one or more target-specific binding moieties which specifically bind to the nucleic acid target molecule, when present. When the linking molecule comprises multiple target-specific binding moieties, each of the target-specific binding moieties specifically binds to a different region of the nucleic acid target molecule when present. The linking molecule also comprises one or more capture probe-specific binding moieties which specifically bind to at least one of the plurality of capture probes. When the linking molecule comprises a single target-specific binding moiety, the linking molecule comprises a plurality of capture probe-specific binding moieties, and when the linking molecule comprises a single capture probe-specific binding moiety, the linking molecule comprises a plurality of target-specific binding moieties. When the nucleic acid target molecule is present in the sample, the linking molecule specifically binds to the nucleic acid target molecule and one or more of the capture probes bound to the substrate, thereby forming a complex comprising the nucleic acid target molecule, the linking molecule and the substrate.

In one embodiment of the reaction mixture described in the seventh aspect of the present disclosure, the substrate comprises a biochip surface.

In another embodiment of the reaction mixture described in the seventh aspect of the present disclosure, the substrate is a detectable label. In one embodiment where the substrate is a detectable label, the substrate is a magnetic particle.

In another embodiment of the reaction mixture described in the seventh aspect of the present disclosure, the linking molecule comprises a plurality of the target-specific binding moieties and one of the capture probe-specific binding moieties.

In another embodiment of the reaction mixture described in the seventh aspect of the present disclosure, the linking molecule comprises one of the target-specific binding moieties and a plurality of the capture probe-specific binding moieties.

In another embodiment of the reaction mixture described in the seventh aspect of the present disclosure, the linking molecule comprises a plurality of the target-specific binding moieties and a plurality of the capture probe-specific binding moieties.

In an eighth aspect of the present disclosure, an embodiment of the reaction mixture described in the seventh aspect is disclosed, wherein the substrate is a detectable label, and wherein the reaction mixture further comprises a substrate comprising a biochip surface, wherein the biochip surface comprises at least one target-immobilization probe bound thereto. When the nucleic acid target molecule is present in the sample, the target-immobilization probe specifically binds to the nucleic acid target molecule, the nucleic acid target molecule specifically binds to the linking molecule and the linking molecule specifically binds to one or more of the capture probes bound to the detectable label, thereby forming a complex comprising the biochip surface, the target-immobilization probe, the nucleic acid target molecule, the linking molecule and the detectable label.

In one embodiment of the reaction mixture described in the eighth aspect of the present disclosure, the detectable label is a magnetic particle.

In another embodiment of the reaction mixture described in the eighth aspect of the present disclosure, the linking molecule comprises a plurality of the target-specific binding moieties and one of the capture probe-specific binding moieties.

In another embodiment of the reaction mixture described in the eighth aspect of the present disclosure, the linking molecule comprises one of the target-specific binding moieties and a plurality of the capture probe-specific binding moieties.

In another embodiment of the reaction mixture described in the eighth aspect of the present disclosure, the linking molecule comprises a plurality of the target-specific binding moieties and a plurality of the capture probe-specific binding moieties.

In a ninth aspect of the present disclosure, an embodiment of the reaction mixture described in the seventh aspect is disclosed, wherein the substrate is a detectable label, and wherein the reaction mixture further comprises a substrate comprising a biochip surface, wherein the biochip surface comprises a plurality of capture probes bound thereto. The reaction mixture also further comprises a second linking molecule, wherein the second linking molecule comprises one or more target-specific binding moieties which specifically bind to the nucleic acid target molecule, when present. When the second linking molecule comprises multiple target-specific binding moieties, each of the target-specific binding moieties specifically binds to a different region of the nucleic acid target molecule when present. The second linking molecule also comprises one or more capture probe-specific binding moieties which specifically bind to at least one of the plurality of capture probes bound to the biochip surface. When the second linking molecule comprises a single target-specific binding moiety, the second linking molecule comprises a plurality of capture probe-specific binding moieties, and when the second linking molecule comprises a single capture probe-specific binding moiety, the second linking molecule comprises a plurality of target-specific binding moieties. When the nucleic acid target molecule is present in the sample, the linking molecule specifically binds to the nucleic acid target molecule and one or more of the capture probes bound to the detectable label, and the second linking molecule specifically binds to the nucleic acid target molecule and one or more of the capture probes bound to the biochip surface, thereby forming a complex comprising the detectable label, the linking molecule, the nucleic acid target molecule, the second linking molecule and the biochip surface.

In one embodiment of the reaction mixture described in the ninth aspect of the present disclosure, the detectable label is a magnetic particle.

In another embodiment of the reaction mixture described in the ninth aspect of the present disclosure, the second linking molecule comprises a plurality of the target-specific binding moieties and one of the capture probe-specific binding moieties.

In another embodiment of the reaction mixture described in the ninth aspect of the present disclosure, the second linking molecule comprises one of the target-specific binding moieties and a plurality of the capture probe-specific binding moieties.

In another embodiment of the reaction mixture described in the ninth aspect of the present disclosure, the second linking molecule comprises a plurality of the target-specific binding moieties and a plurality of the capture probe-specific binding moieties.

In a tenth aspect, the present disclosure provides a reaction mixture comprising a substrate, wherein the substrate comprises a plurality of capture probe bound thereto; a sample suspected of containing a nucleic acid target molecule; and a plurality of linking molecules. Each member of the plurality of linking molecules is independently present in one or more copies, and each member comprises a target-specific binding moiety which specifically binds to a different region of the nucleic acid target molecule, when present. Each member of the plurality of linking molecules also comprises a capture probe-specific binding moiety which specifically binds to a capture probe of the plurality of capture probes. When the nucleic acid target molecule is present in the sample, the plurality of linking molecules specifically binds to a plurality of different regions of the nucleic acid target molecule and a plurality of the capture probes bound to the substrate, thereby forming a complex comprising the nucleic acid target molecule, the plurality of linking molecules, and the substrate.

In one embodiment of the reaction mixture described in the tenth aspect of the present disclosure, the substrate comprises a biochip surface. In another embodiment, the substrate is a detectable label. In one embodiment where the substrate is a detectable label, the substrate is a magnetic particle.

In an eleventh aspect, the present disclosure provides a reaction mixture as described in the tenth aspect, wherein the substrate is a detectable label, and wherein the reaction mixture further comprises a substrate comprising a biochip surface. The biochip surface comprises at least one target-immobilization probe bound thereto. When the nucleic acid target molecule is present in the sample, the target-immobilization probe specifically binds to the nucleic acid target molecule, the nucleic acid target molecule specifically binds to the plurality of linking molecules and the plurality of linking molecules specifically binds to a plurality of the capture probes bound to the detectable label, thereby forming a complex comprising the biochip surface, the target-immobilization probe, the nucleic acid target molecule, the plurality of linking molecules and the detectable label.

In one embodiment of the reaction mixture described in the eleventh aspect of the present disclosure, the detectable label is a magnetic particle.

In a twelfth aspect, the present disclosure provides a reaction mixture as described in the tenth aspect, wherein the substrate is a detectable label, and wherein the reaction mixture further comprises a substrate comprising a biochip surface, wherein the biochip surface comprises a plurality of capture probes bound thereto. The reaction mixture also further comprises a second plurality of linking molecules, wherein each member of the second plurality of linking molecules is independently present in one or more copies. Each member of the second plurality of linking molecules comprises a target-specific binding moiety which specifically binds to a different region of the nucleic acid target molecule, when present. Each member of the second plurality of linking molecules also comprises a capture probe-specific binding moiety which specifically binds to a capture probe of the plurality of capture probes bound to the biochip surface. When the nucleic acid target molecule is present in the sample, the plurality of linking molecules specifically binds to the nucleic acid target molecule and a plurality of the capture probes bound to the detectable label, and the second plurality of linking molecules specifically binds to the nucleic acid target molecule and a plurality of the capture probes bound to the biochip surface, thereby forming a complex comprising the detectable label, the plurality of linking molecules, the nucleic acid target molecule, the second plurality of linking molecules and the biochip surface.

In one embodiment of the reaction mixture described in the twelfth aspect of the present disclosure, the detectable label is a magnetic particle.

Kits are also described herein. For example, a kit comprising a detectable particle and a linking molecule is described, wherein the detectable particle comprises a plurality of capture probes bound thereto, and the linking molecule comprises one or more target-specific binding moieties which specifically bind to a nucleic acid target molecule, when present. When the linking molecule comprises multiple target-specific binding moieties, each of the target-specific binding moieties specifically binds to a different region of the nucleic acid target molecule when present. The linking molecule also comprises one or more capture probe-specific binding moieties which specifically bind to at least one of the plurality of capture probes. When the linking molecule comprises a single target-specific binding moiety, the linking molecule comprises a plurality of capture probe-specific binding moieties, and when the linking molecule comprises a single capture probe-specific binding moiety, the linking molecule comprises a plurality of target-specific binding moieties. The detectable particle can be a magnetic particle.

In one embodiment, the kit further comprises a substrate comprising a biochip surface, wherein the biochip surface comprises at least one target-immobilization probe bound thereto, and wherein the target-immobilization probe specifically binds the nucleic acid target molecule when present.

In another embodiment, a kit comprising a detectable particle and a plurality of linking molecules is described, wherein the detectable particle comprises a plurality of capture probes bound thereto. Each member of the plurality of linking molecules is independently present in one or more copies, and each member comprises a target-specific binding moiety which specifically binds to a different region of said nucleic acid target molecule, when present, and a capture probe-specific binding moiety which specifically binds to a capture probe of the plurality of capture probes. In one such embodiment, the kit further comprises a substrate comprising a biochip surface, wherein the biochip surface comprises at least one target-immobilization probe bound thereto, and wherein the target-immobilization probe specifically binds the nucleic acid target molecule when present. In another embodiment, the kit comprises a substrate comprising a biochip surface, wherein the biochip surface comprises a plurality of capture probes bound thereto and a second plurality of linking molecules. Each member of said second plurality of linking molecules is independently present in one or more copies, and each member comprises a target-specific binding moiety which specifically binds to a different region of said nucleic acid target molecule, when present, and a capture probe-specific binding moiety which specifically binds to a capture probe of the plurality of capture probes bound to the biochip surface. When the nucleic acid target molecule is present in the sample, the plurality of linking molecules specifically binds to said nucleic acid target molecule and a plurality of the capture probes bound to the detectable label, and the second plurality of linking molecules specifically binds to the nucleic acid target molecule and a plurality of the capture probes bound to the biochip surface, thereby forming a complex comprising the detectable label, the plurality of linking molecules, the nucleic acid target molecule, the second plurality of linking molecules and the biochip surface. In one embodiment, the detectable particle is a magnetic particle.

BRIEF DESCRIPTION OF THE DRAWINGS

The disclosure is best understood from the following detailed description when read in conjunction with the accompanying drawings. It is emphasized that, according to common practice, the various features of the drawings are not necessarily to-scale. The dimensions of the various features are arbitrarily expanded or reduced for clarity. Included in the drawings are the following figures.

DEFINITIONS

Figure 1:
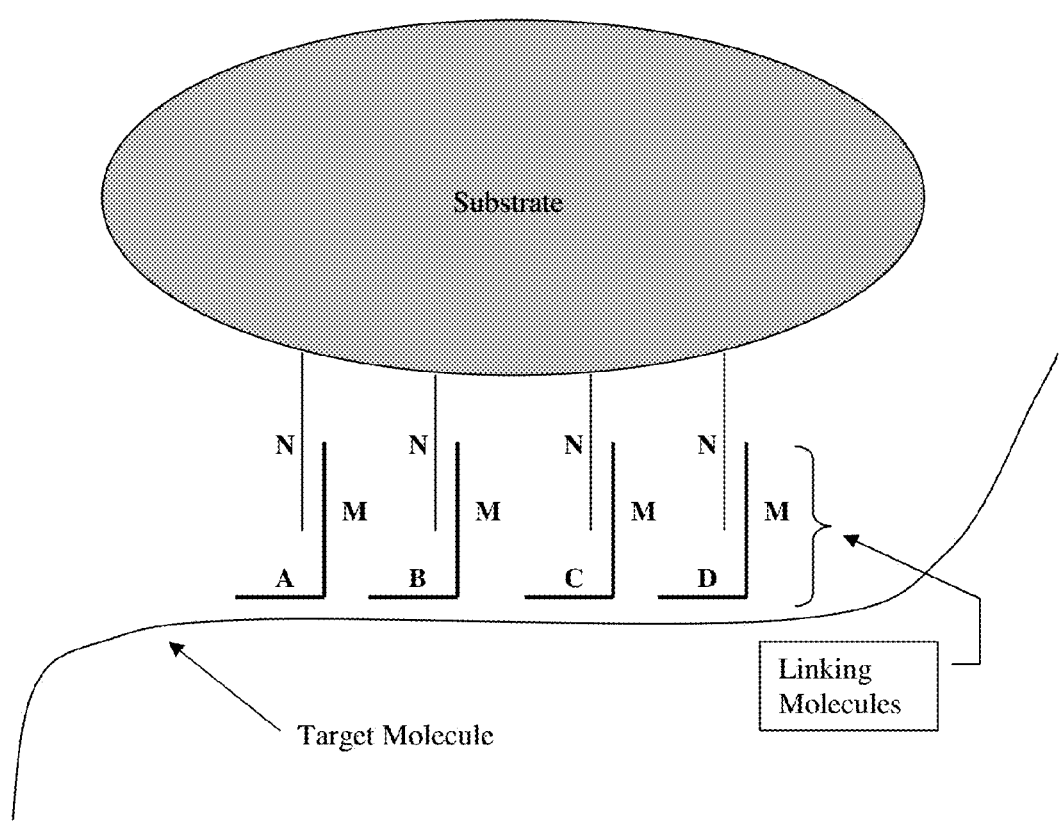
FIG. 1 provides an illustration of a binding complex involving a capture probe functionalized substrate, a target molecule and a plurality of linking molecules. The illustration of FIG. 1 depicts the substrate as a substrate comprising a detectable label.

Depending on the context, the term "substrate" as used herein refers to a substrate that can serve as a detectable label (or be modified to serve as a detectable label), e.g., a magnetic particle, or a substrate comprising a biochip surface which can be used to immobilize a target molecule for subsequent detection.

As used herein the term "biochip" refers to a solid, normally substantially planar support having a surface that is functionalized with an array of biological molecules capable of binding to other biological molecules of interest. A variety of materials can be used in the preparation of biochips including, e.g., glass slides, fused silica, silicon and plastic. In particular embodiments disclosed herein, biochips of interest comprise magnetic sensors capable of detecting the presence of a magnetic particle bound to a target molecule immobilized on the surface of the biochip. See, for example, Baselt et al., (1998) Biosens. Bioelectron., vol. 13, pp. 731-739; Edelstein et al., (2000) Biosens. Bioelectron., vol. 14, pp. 805-813; Miller et al., (2001) J. Magn. Magn. Mater., vol. 225, pp. 138-144; Graham et al. (2002) J. Appl. Phys., vol. 91, pp. 7786-7788; Ferreira et al. (2003) J. Appl. Phys., vol. 93, pp. 7281; Li et al. (2003) J. Appl. Phys., vol. 93, pp. 7557-7559, May; Li et al. (2004) IEEE Trans. Magn., vol. 40, pp. 3000; Wang et al., (2005) J. Magn. Magn. Mater., vol. 293, pp. 731-736; Shen et al. (2005) Appl. Phys. Lett., vol. 86, pp. 253901; Baselt et al. U.S. Pat. No. 5,981,297; Tondra, U.S. Pat. No. 6,743,639; and Tondra U.S. Pat. No. 6,875,621.

As used herein, the term "detectable label" refers to a molecule or particle capable of detection, including, but not limited to, radioactive isotopes, fluorescers, chemiluminescers, enzymes, enzyme substrates, enzyme cofactors, enzyme inhibitors, chromophores, dyes, metal ions, magnetic particles, members of a specific binding pair and the like.

The term "linking molecule" is used herein to refer to a molecule comprising at least one "capture probe-specific binding moiety" and at least one "target-specific binding moiety." The word "molecule" when used in the context of a linking molecule is not limited to a single molecular entity and can include a plurality of molecules bound to one another to produce the linking molecule.

The term "target-specific binding moiety" is used herein to refer a region of a linking molecule that is capable of specifically binding to a target molecule or other analyte of interest when brought into contact with the target molecule or other analyte of interest.

The term "capture probe-specific binding moiety" is used herein to refer to a region of a linking molecule that is capable of specifically binding to a "capture probe" when brought into contact with the capture probe.

The term "capture probe" is used herein to refer to an entity bound to a substrate, wherein the entity is capable of specifically binding to a capture probe-specific binding moiety of a linking molecule when brought into contact with the linking molecule. For example, in one embodiment, a capture probe-specific binding moiety comprises a nucleic acid sequence and the corresponding capture probe comprises a sequence complementary to that sequence such that the capture probe is capable of specifically hybridizing with the capture probe-specific binding moiety.

The term "target-immobilization probe" is used herein to refer to an entity bound to a surface of a substrate, e.g., a biochip, wherein the entity is capable of specifically binding to a target molecule when brought into contact with the target molecule.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and native leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like.

The terms "nucleic acid," "nucleic acid molecule" and "polynucleotide" are used interchangeably and refer to a polymeric form of nucleotides of any length, either deoxyribonucleotides or ribonucleotides, or compounds produced synthetically which can hybridize with naturally occurring nucleic acids in a sequence specific manner similar to that of two naturally occurring nucleic acids, e.g., can participate in Watson-Crick base pairing interactions. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, cDNA, recombinant polynucleotides, plasmids, vectors, isolated DNA of any sequence, control regions, isolated RNA of any sequence, nucleic acid probes, and primers.

The term "moiety" is used to refer to a portion of an entity or molecule, typically having a particular functional or structural feature.

The terms "antibody," "immunoglobulin" and their plural referents include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like. Also encompassed by the terms are Fab', Fv, F(ab')2, and or other antibody fragments that retain specific binding to antigen.

Antibodies can be in a variety of forms including, for example, Fv, Fab, and (Fab')2, as well as bi-functional (i.e. bi-specific) hybrid antibodies (e.g., Lanzavecchia et al., *Eur. J. Immunol.* 17, 105 (1987)) and in single chains (e.g., Huston et al., Proc. Natl. Acad. Sci. U.S.A., 85, 5879-5883 (1988); Bird et al., Science, 242, 423-426 (1988); see Hood et al., "Immunology", Benjamin, N.Y., 2nd ed. (1984), and Hunkapiller and Hood, *Nature,* 323, 15-16 (1986)).

The terms "specific binding," "specifically bind," and the like, refer to the ability of a first binding molecule or moiety (e.g., a target-specific binding moiety or first member of a specific binding pair) to preferentially bind (covalently or non-covalently) to a second binding molecule or moiety (e.g., a target molecule or second member of a specific binding pair) relative to other molecules or moieties in a reaction mixture. For example, in certain embodiments involving protein-protein binding interactions, the affinity between a first binding molecule or moiety and a second binding molecule or moiety when they are specifically bound to each other in a binding complex is characterized by a KD (dissociation constant) of less than $10^{-6}$M, less than $10^{-7}$M, less than $10^{-8}$M, less than $10^{-9}$M, less than $10^{-10}$M, less than $10^{-11}$M, less than $10^{-12}$M, less than $10^{-13}$M, less than $10^{-14}$M, or less than $10^{-15}$M.

As used herein, a "member of a specific binding pair" is a member of a specific binding pair interaction. It should be noted that when either member of the binding pair is referred to as the first member, the remaining member is understood to be the second member and vice versa. Examples of specific binding pair interactions include immune binding interactions such as antigen/antibody and hapten/antibody as well as non-immune binding interactions such as complementary nucleic acid binding, biotin/avidin and biotin/streptavidin. As used herein, "member of a specific binding pair" is also used to refer to a member of a reactive pair, wherein the members of the reactive pair are capable of forming one or more covalent bonds with each other. Examples of covalent bond forming reactive pairs include Cu-catalyzed azide/alkyne [3+2] cycloaddition "click chemistry" as described by Rostovtsev et al. (2002) *Angew. Chem. Int. Ed.* 41: 2596-2599 and Tornoe et al. (2002) *J. Org. Chem.* 67: 3057-3064; azide/DIFO (Difluorinated Cyclooctyne) Cu-free click chemistry as described by Baskin et al. (2007) *PNAS* Vol. 104, No. 43: 167393-16797; azide/phosphine "Staudinger Reaction" as described by Lin et al. (2005) *J. Am. Chem. Soc.* 127: 2686-2695; azide/triarylphosphine "Modified Staudinger Reaction" as described by Saxon and Bertozzi (2000) Mar. 17 *Science* 287(5460):2007-10; and catalyzed olefin cross metathesis reactions as described by Casey (2006) *J. of Chem. Edu*. Vol. 83, No. 2: 192-195, Lynn et al. (2000) *J. Am. Chem. Soc.* 122: 6601-6609, and Chen et al. (2003) *Progress in Chemistry* 15: 401-408.

The terms "capable of hybridizing," "hybridizing" and "hybridization" as used herein refer to a "specific binding" interaction between complementary or partially complementary nucleic acid molecules (e.g., DNA-DNA, RNA-DNA, RNA-RNA).

The term "complementary" references a property of specific binding between polynucleotides based on the sequences of the polynucleotides. As used herein, polynucleotides are complementary if they bind to each other in a hybridization assay under stringent conditions, e.g. if they produce a given or detectable level of signal in a hybridization assay. Portions of polynucleotides are complementary to each other if they follow conventional base-pairing rules, e.g. A pairs with T (or U) and G pairs with C. "Complementary" includes embodiments in which there is an absolute sequence complementarity, and also embodiments in which there is a substantial sequence complementarity.

"Absolute sequence complementarity" means that there is 100% sequence complementarity between a first polynucleotide and a second polynucleotide, i.e. there are no insertions, deletions, or substitutions in either of the first and second polynucleotides with respect to the other polynucleotide (over the complementary region). Put another way, every base of the complementary region is paired with its complementary base following normal base-pairing rules.

"Substantial sequence complementarity" permits one or more relatively small (less than 10 bases, e.g. less than 5 bases, typically less than 3 bases, more typically a single base) insertions, deletions, or substitutions in the first and or second polynucleotide (over the complementary region) relative to the other polynucleotide. The complementary region is the region that is complementary between a first polynucleotide and a second polynucleotide (e.g. a distinct sequence of a nucleic acid target molecule and a binding moiety of a linking molecule). Complementary sequences are typically embedded within larger polynucleotides, thus two relatively long polynucleotides may be complementary over only a portion of their total length. The complementary region is typically at least about 10 bases long, more typically at least about 12 bases long, more typically at least about 15 bases long, still more typically at least about 20 bases long, or may be at least about 25 bases long.

Hybridization as described herein in the context of nucleic acid hybridization typically occurs under "stringent conditions." The term "stringent conditions" refers to conditions under which a first nucleic acid will hybridize preferentially to a second nucleic acid sequence, and to a lesser extent to, or not at all to, other sequences. Put another way, the term "stringent hybridization conditions" as used herein refers to conditions that are compatible to produce duplexes between complementary binding members, e.g., between a binding moiety of a linking molecule and a complementary sequence of a target nucleic acid.

"Stringent hybridization conditions" and "stringent hybridization wash conditions" in the context of nucleic acid hybridization (e.g., as in array, Southern or Northern hybridizations) are sequence dependent, and are different under different environmental parameters. Stringent hybridization conditions can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C. Alternatively, hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. can be employed. Yet additional stringent hybridization conditions include hybridization at 60° C. or higher and 3×SSC (450 mM sodium chloride/45 mM sodium citrate) or incubation at 42° C. in a solution containing 30% formamide, 1M NaCl, 0.5% sodium sarcosine, 50 mM MES, pH 6.5. Those of ordinary skill will readily recognize that alternative but comparable hybridization and wash conditions can be utilized to provide conditions of similar stringency.

In certain embodiments, the stringency of the wash conditions may affect the degree to which nucleic acid molecules specifically hybridize. Suitable wash conditions may include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2× SSC at a temperature of at least about 50° C. or about 55° C. to about 60° C. for about 1 to about 20 minutes; or, multiple washes with a solution with a salt concentration of about 0.1×SSC containing 0.1% SDS at 20 to 50° C. for 1 to 15 minutes; or, equivalent conditions. Stringent conditions for washing can also be, e.g., 0.2×SSC/0.1% SDS at 42° C. In instances wherein the nucleic acid molecules are oligodeoxynucleotides (e.g. oligonucleotides made up of deoxyribonucleotide subunits), stringent conditions can include washing in 6×SSC/0.05% sodium pyrophosphate at 37° C. (for 14-base oligos), 48° C. (for 17-base oligos), 55° C. (for 20-base oligos), and 60° C. (for 23-base oligos). See Sambrook, et al., *Molecular Cloning: A Laboratory Manual*, Second Edition, (1989) Cold Spring Harbor, N.Y.), for detailed descriptions of equivalent hybridization and wash conditions and for reagents and buffers, e.g., SSC buffers and equivalent reagents and conditions.

Stringent hybridization conditions may also include a "prehybridization" of aqueous phase nucleic acids with complexity-reducing nucleic acids to suppress repetitive sequences. For example, certain stringent hybridization conditions include, prior to any hybridization to surface-bound polynucleotides, hybridization with Cot-1 DNA or with random sequence synthetic oligonucleotides (e.g. 25-mers), or the like.

Stringent hybridization conditions are hybridization conditions that are at least as stringent as the above representative conditions, where conditions are considered to be at least as stringent if they are at least about 80% as stringent, typically at least about 90% as stringent as the above specific stringent conditions. Other stringent hybridization conditions are known in the art and may also be employed, as appropriate.

The terms "bind" and "bound" as used herein refers to a binding interaction between two or more entities. Where two entities, e.g., molecules, are bound to each other, they may be "directly bound," e.g., through covalent bonds, ionic bonds, hydrogen bonds, electrostatic interactions, hydrophobic interactions, Van der Waals forces, or a combination thereof, or they may be "indirectly bound," e.g., through the use of an intermediate linking moiety.

The terms "detect", "detecting" and the like encompass quantitative as well as qualitative measurements.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. It should be noted that the use of the term "preferred" in this context is not intended to limit the scope of the invention in any way. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "a linking molecule" includes a plurality of such linking molecules and reference to "the binding complex" includes reference to one or more binding complexes and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The following detailed description is put forth so as to provide those of ordinary skill in the art with a complete disclosure and description of how to make and use the present invention, and is not intended to limit the scope of what the inventors regard as their invention. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s) and the like.

DETAILED DESCRIPTION

The present disclosure is directed to methods and compositions which can be used to increase the strength of and/or probability of forming a binding complex comprising a target molecule and a substrate. In one aspect, linking molecules are disclosed which can be used to increase the number of intra-complex binding interactions. Covalent bonds can be introduced to further increase the binding strength of these intra-complex binding interactions. Inter-complex cross-linking, i.e., cross-linking of two-or more different binding complexes, can be utilized in connection with these methods to further strengthen and stabilize the disclosed binding complexes.

Creating a Target Molecule-Substrate Complex Having Multiple Intra-Complex Binding Interaction Sites In one aspect, the present disclosure is directed to methods and compositions which may be utilized to create binding complexes comprising a target molecule and one or more substrates, wherein the binding complexes have multiple intra-complex binding interaction sites. One or more linking molecules are utilized to create the multiple intra-complex binding interaction sites in the target molecule-substrate binding complexes. In some embodiments, one or more linking molecules are used to provide multiple intra-complex binding interaction sites in a binding complex comprising a target molecule and a detectable label. In other embodiments, one or more linking molecules are used to provide multiple intra-complex binding interaction sites in a binding complex comprising a target molecule and a biochip surface. These embodiments can be employed either separately or together in a particular assay, e.g., an assay designed to detect the presence, absence and/or quantity of a target molecule.

Where one or more linking molecules are used to provide multiple intra-complex binding interaction sites in a binding complex comprising a target molecule and a detectable label, the linking molecules may be designed such that one or more detectable label entities bind the target molecule via the linking molecule or molecules. For example, in one embodiment only a single detectable label entity, e.g., a single magnetic particle, is bound to a particular target molecule via the linking molecule or molecules. In other embodiments, multiple detectable label entities are bound to a particular target molecule via the linking molecule or molecules.

A variety of molecular targets may be utilized in connection with the presently disclosed methods and compositions including, but not limited to, nucleic acid targets.

Nucleic Acid Linking Molecules

Where the target molecule is a nucleic acid, nucleic acid linking molecules can be used to form a nucleic acid target molecule-substrate complex having multiple intra-complex binding sites. In one aspect of the present disclosure, a plurality of nucleic acid linking molecules is disclosed, wherein each nucleic acid linking molecule of the plurality of nucleic acid linking molecules comprises two different binding moieties. The first binding moiety, a target-specific binding moiety, comprises a nucleic acid sequence capable of hybridizing specifically to a distinct sequence of the nucleic acid target molecule. The second binding moiety, a capture probe-specific binding moiety, comprises a nucleic acid sequence capable of hybridizing specifically to a sequence of a nucleic acid molecule bound to a substrate as a capture probe. Generally, the substrate comprises a plurality of such nucleic acid capture probes bound thereto. The plurality of linking molecules is designed such that it is capable of binding to a plurality of different regions of the target molecule and a plurality of the capture probes bound to the substrate. In this manner, a nucleic acid target molecule-substrate complex having multiple intra-complex binding sites can be formed.

Figure 2:
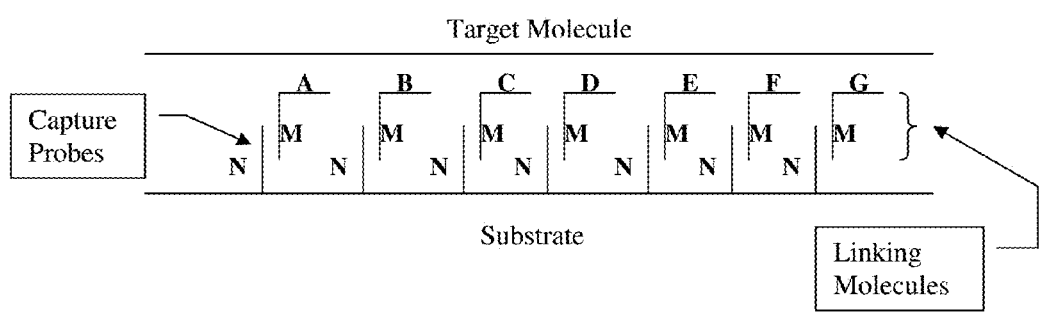
FIG. 2 provides an illustration of a binding complex involving a capture-probe functionalized substrate, a target molecule and a plurality of linking molecules. The illustration of FIG. 2 depicts the substrate as a substrate comprising a biochip surface.

FIGS. 1 and 2 illustrate binding interactions utilizing specific embodiments of the nucleic acid linking molecules disclosed herein.

FIG. 1 shows an embodiment in which the substrate is a detectable label, e.g., a magnetic particle. As illustrated in FIG. 1, the plurality of nucleic acid linking molecules can be designed such that members of the plurality bind to the same substrate while members of the plurality bind to different sequences of the nucleic acid target molecule. This results in the formation of a target molecule-substrate binding complex having multiple intra-complex binding interaction sites. In FIG. 1, each of "A-D" represent a different target-specific binding moiety, each "M" represents a capture-probe specific binding moiety, and each "N" represents a nucleic acid molecule bound to the substrate as a capture probe. In the specific embodiment of FIG. 1, each of binding moieties "A-D" comprise a different nucleic acid sequence relative to one another, each "M" comprises the same nucleic acid sequence relative to each other "M," and each "N" comprises the same nucleic acid sequence relative each other "N." In this embodiment, "M" and "N" comprise complementary sequences.

FIG. 2 shows an embodiment in which the substrate comprises a surface of a biochip. In this embodiment, the plurality of nucleic acid linking molecules facilitates the formation of a target molecule-biochip substrate binding complex having a plurality intra-complex binding interaction sites.

In FIG. 2, each of "A-G" represents a different target-specific binding moiety, each "M" represents a capture-probe specific binding moiety, and each "N" represents a nucleic acid molecule bound to the substrate as a capture probe. In the embodiment of FIG. 2, each of binding moieties "A-G" comprise a different nucleic acid sequence relative to one another, each "M" comprises the same nucleic acid sequence relative to each other "M," and each "N" comprises the same nucleic acid sequence relative to each other "N." In this embodiment, "M" and "N" comprise complementary sequences.

Thus, in some aspects of the present disclosure, the linking molecules can be considered to translate the heterogeneous sequence sections on a target molecule to become multiple sites of identical sequence complementary to nucleic acid molecules bound to a substrate. This increases the probability that the substrate will bind to the target molecules, thereby allowing more efficient binding of the substrate.

Figure 6A:
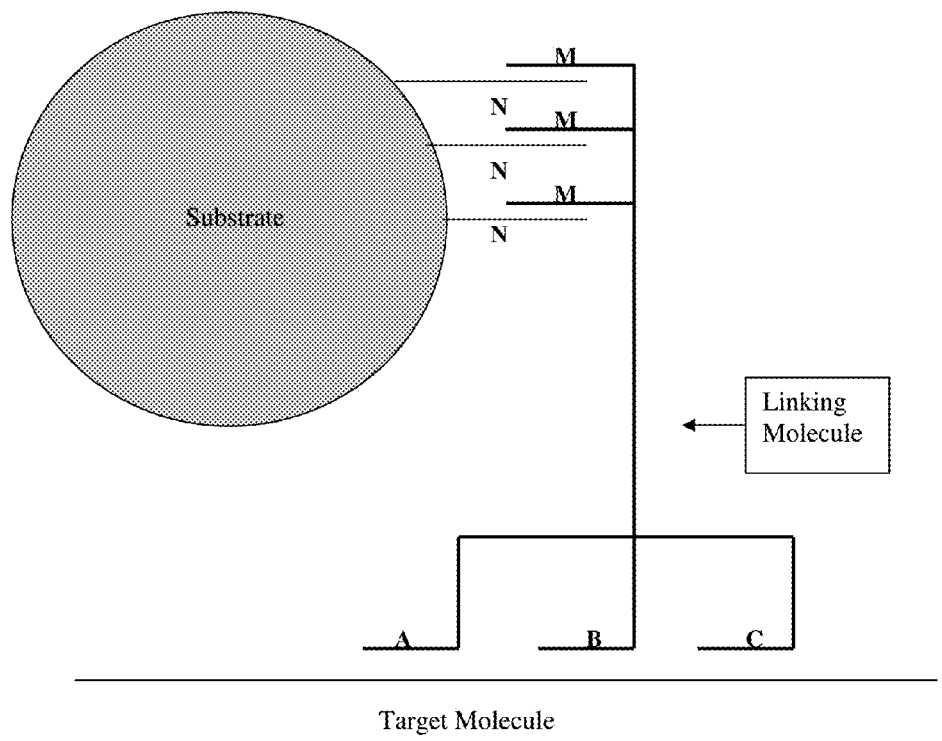
FIG. 6A provides an illustration of a binding complex involving a capture probe functionalized substrate, a target molecule and a linking molecule, wherein the linking molecule comprises a plurality of target specific binding moieties and a plurality of capture probe-specific binding moieties FIG. 6B provides an illustration of a binding complex involving a first plurality of linking molecules (L1), a capture probe (C1) functionalized detectable label, a target molecule, a second plurality of linking molecules (L2), and a capture probe (C2) functionalized substrate comprising a biochip surface.
Figure 6B:
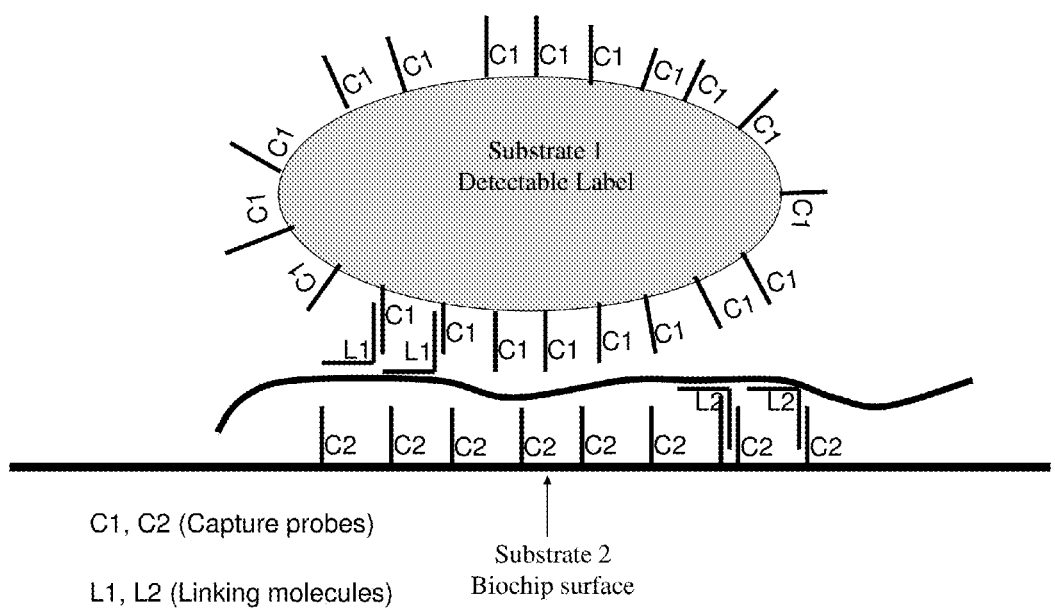

As illustrated in FIG. 6B, linking molecules described herein can be utilized to form a binding complex comprising a nucleic acid target molecule and two different functionalized substrates, e.g., detectable label substrate and a substrate comprising a biochip surface.

In some embodiments, the plurality of linking molecules is contacted to the target molecule (or a sample suspected of containing the target molecule) prior to contacting with the substrate so that the positioning of the linking molecules relative to the target molecule, prior to binding with the target molecule, is not significantly affected by the positions at which the linking molecules bind the substrate via the capture probes. A simplified version of this concept can be seen by reference to FIG. 1, wherein the order of "A-D" with respect to the target molecule is maintained by contacting the plurality of linking molecules to the target molecule prior to contacting the plurality of linking molecules with the substrate.

In another aspect of the present disclosure, a nucleic acid linking molecule is disclosed, wherein the nucleic acid linking molecule comprises a target-specific binding moiety and a plurality of capture probe-specific binding moieties. The target-specific binding moiety is capable of hybridizing specifically to a distinct sequence of a nucleic acid target molecule and each member of the plurality of capture probe-specific binding moieties is capable of hybridizing specifically to a nucleic acid molecule of a plurality of nucleic acid molecules bound to a substrate as capture probes. In this manner, the linking molecule is capable of binding the target molecule and a plurality of nucleic acid capture probes bound to the substrate.

Figure 3:
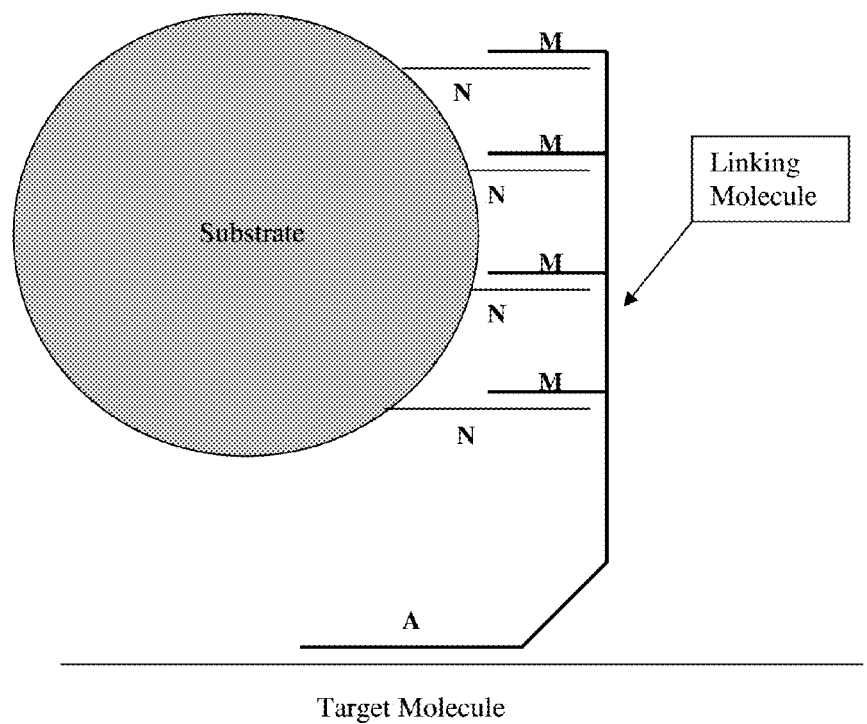
FIG. 3 provides an illustration of a binding complex involving a capture probe functionalized substrate, a target molecule and a linking molecule, wherein the linking molecule comprises a target specific binding moiety and a plurality of capture probe-specific binding moieties. The illustration of FIG. 3 depicts a linking molecule in a branched configuration.
Figure 4:
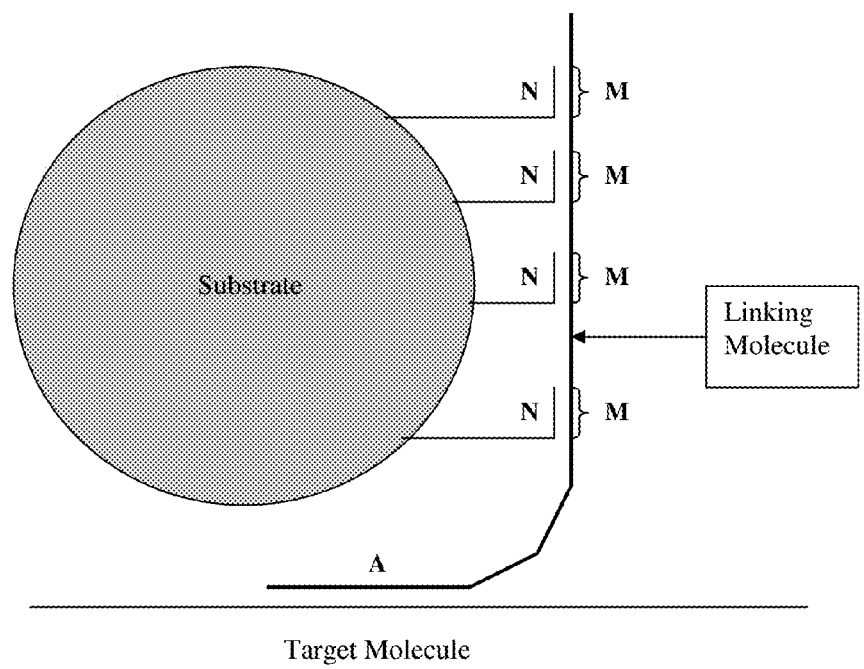
FIG. 4 provides an illustration of a binding complex involving a capture probe functionalized substrate, a target molecule and a linking molecule, wherein the linking molecule comprises a target specific binding moiety and a plurality of capture probe-specific binding moieties. The illustration of FIG. 4 depicts a linking molecule in a linear configuration.

FIGS. 3 and 4 illustrate binding interactions utilizing specific embodiments of the nucleic acid linking molecules disclosed herein.

FIG. 3 shows an example of a nucleic acid linking molecule having a branched configuration. In FIG. 3, "A" represents the target-specific binding moiety, each "M" represents a capture-probe specific binding moiety, and each "N" represents a nucleic acid molecule bound to the substrate as a capture probe. In the embodiment pictured in FIG. 3, each "M" comprises the same nucleic acid sequence relative to each other "M", and each "N" comprises the same nucleic acid sequence relative to each other "N." In this embodiment, "M" and "N" comprise complementary sequences.

FIG. 4 shows an example of a nucleic acid linking molecule having a linear configuration. In FIG. 4, "A" represents the target-specific binding moiety, each "M" represents a capture-probe specific binding moiety, and each "N" represents a nucleic acid molecule of a plurality of nucleic acid molecules bound to the substrate as capture probes. In the embodiment pictured in FIG. 4, each "M" comprises the same nucleic acid sequence relative to each other "M", and each "N" comprises the same nucleic acid sequence relative to each other "N." In this embodiment, "M" and "N" comprise complementary sequences.

In another aspect of the present disclosure, a nucleic acid linking molecule is disclosed wherein the nucleic acid linking molecule comprises a capture probe-specific binding moiety and a plurality of target-specific binding moieties. The capture probe-specific binding moiety comprises a nucleic acid sequence capable of hybridizing specifically to a nucleic acid molecule bound to a substrate as a capture probe. In addition, each member of the plurality of target-specific binding moieties comprises a nucleic acid sequence capable of hybridizing specifically to a different nucleic acid sequence of a nucleic acid target molecule.

Figure 5:
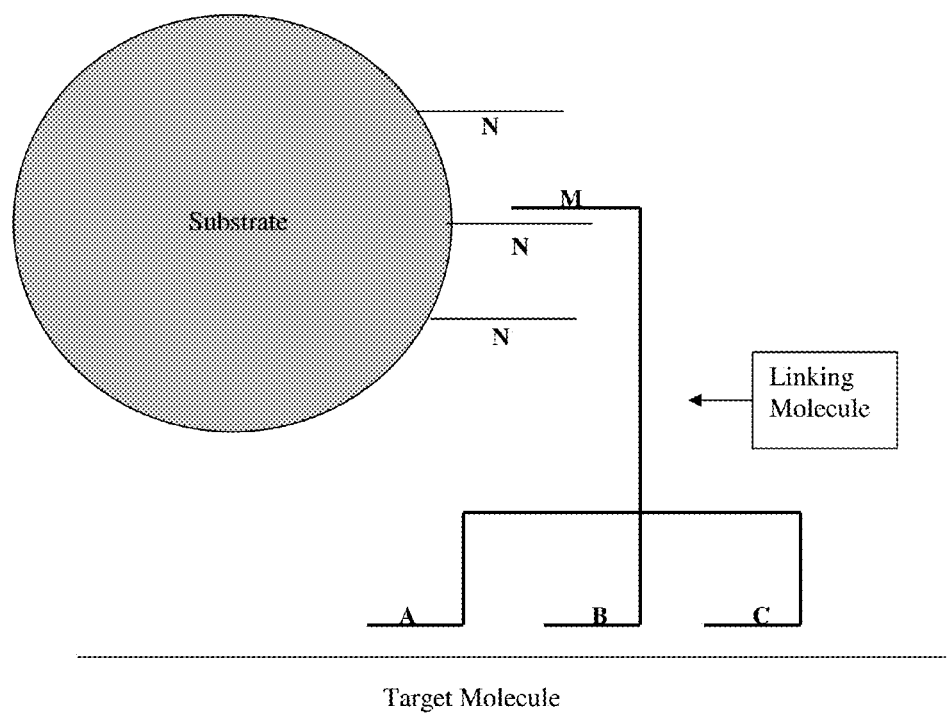
FIG. 5 provides an illustration of a binding complex involving a capture-probe functionalized substrate, a target molecule and a linking molecule, wherein the linking molecule comprises a plurality of target specific binding moieties and a capture probe-specific binding moiety.

FIG. 5 illustrates binding interactions utilizing a specific embodiment of this linking molecule. FIG. 5 shows a branched linking molecule, wherein "M" represents the capture-probe specific binding moiety, "N" represents a nucleic acid molecule bound to a substrate as a capture probe, and "A-C" represent the plurality of target-specific binding moieties. In the embodiment pictured in FIG. 5, "M" and "N" comprise complementary sequences. Although FIG. 5 depicts a branched linking molecule, the embodiment shown in FIG. 5 can also be prepared in a linear configuration.

In another aspect of the present disclosure, a nucleic acid linking molecule is disclosed wherein the nucleic acid linking molecule comprises a plurality of capture probe-specific binding moieties and a plurality of target-specific binding moieties. The capture probe-specific binding moieties comprise nucleic acid sequences capable of hybridizing specifically to nucleic acid molecules bound to a substrate as capture probes. In addition, each member of the plurality of target-specific binding moieties comprises a nucleic acid sequence capable of hybridizing specifically to a different nucleic acid sequence of a nucleic acid target molecule.

FIG. 6A illustrates binding interactions utilizing a specific embodiment of this linking molecule. FIG. 6A shows a branched linking molecule, wherein each "M" represents a capture-probe specific binding moiety, each "N" represents a nucleic acid molecule bound to a substrate as a capture probe, and "A-C" represent the plurality of target-specific binding moieties. In the embodiment pictured in FIG. 6A, each "M" comprises the same nucleic acid sequence relative to each other "M", and each "N" comprises the same nucleic acid sequence relative to each other "N." In this embodiment, "M" and "N" comprise complementary sequences. Although FIG. 6A depicts a branched linking molecule, the embodiment shown in FIG. 6A can also be prepared in a linear configuration.

As an alternative to utilizing sequence-based hybridization as the mechanism of binding between a capture probe specific binding moiety and a capture probe bound to a substrate, the linking molecules disclosed herein can be designed to make use of additional specific, non-covalent binding interactions, e.g., biotin or biotin analogues/avidin or streptavidin, haptens/antibodies or antibody fragments, saccharides/lectins and specific ligands/receptors.

Preparation of Nucleic Acid Linking Molecules

The binding moieties of the presently disclosed linking molecules can comprise DNA, RNA, their analogues, modified nucleotides or combinations thereof.

The binding moieties of the linking molecules can be covalently linked directly to each other through phosphodiester bonds or through one or more linking agents such as nucleic acid, amino acid, carbohydrate or polyol bridges, or through other cross-linking agents that are capable of cross-linking nucleic acid or modified nucleic acid strands. The site(s) of linkage can be at the ends of the binding moieties and/or at one or more internal nucleotides in the strand.

The binding moieties of the presently disclosed linking molecules can comprise nucleic acid sequences of about 10 to about 80 nucleotides in length. For example, the first and/or second binding moieties can comprise nucleic acid sequences of about 10 to about 20, about 20 to about 30, about 30 to about 40, about 40 to about 50, about 50 to about 60, about 60 to about 70, or about 70 to about 80 nucleotides in length. More typically, the first and/or second binding moieties of the presently disclosed linking molecules comprise sequences of about 10 to about 60 nucleotides in length, even more typically about 10 to about 45 nucleotides in length.

Nucleic acid molecules bound to a substrate as capture probes are typically from about 10 to about 80 bases in length. For example, the nucleic acid molecules conjugated to the particle labels can be about 10 to about 20, about 20 to about 30, about 30 to about 40, about 40 to about 50, about 50 to about 60, about 60 to about 70, or about 70 to about 80 nucleotides in length. More typically, the nucleic acid molecules conjugated to the particle labels are about 10 to about 60 nucleotides in length, even more typically about 10 to about 45 nucleotides in length.

Where a disclosed linking molecule comprises a plurality of target-specific binding moieties, this plurality can include, e.g., 2 or more, 3 or more, 4 or more, 5 or more, 6 or more, 7 or more, 8 or more, 9, or more, or 10 or more target-specific binding moieties.

Where a disclosed linking molecule comprises a plurality of capture probe-specific binding moieties, this plurality can include e.g., 2 or more, 3 or more, 4 or more, 5 or more, 6 or more, 7 or more, 8 or more, 9, or more, or 10 or more capture probe-specific binding moieties.

In some embodiments, the nucleic acid linking molecules disclosed herein are prepared in a linear configuration, e.g., as illustrated in FIGS. 1 and 4. Linear nucleic acid linking molecules can be prepared using a variety of techniques known in the art. For example, the linking molecules can be prepared by using, polymerase amplification (e.g., PCR), cloning techniques, chemical cross-linking, enzymatic assembly, direct chemical synthesis, or combinations thereof.

Where nucleic linking molecules are prepared by polymerase amplification and/or cloning, nucleic acid sequences that encode the entire linking molecule or fragments thereof can be made in single- or double-stranded form by conventional procedures. When made in double-stranded form, the linking molecules and/or fragments thereof are ultimately denatured or hydrolyzed by single strand exonuclease to provide single-stranded linking molecules and/or fragments thereof. Nucleic acid linking molecules can also be cloned in single-stranded form using conventional single-stranded phage vectors such as M13. Fragments can be linked enzymatically or chemically to form the linking molecule. When assembled enzymatically, the individual fragments can be ligated with a ligase such as T4 DNA or RNA ligase. When prepared by chemical cross-linking, the individual fragments can be synthesized with one or more nucleic acids that have been derivatized to have functional groups that provide linking sites or the fragments can be derivatized after the fragments have been synthesized to provide such sites.

The linking molecules of the present disclosure can also be designed and constructed in a branched configuration as illustrated in FIGS. 3, 5 and 6. Branched linking molecules are differentiated from linear linking molecules in that branched linking molecules have at least 3 termini, which can be 5' termini, 3' termini or a combination thereof. Methods of preparing branched nucleic acid molecules are provided in U.S. Pat. No. 5,124,246, issued Jun. 23, 1992, columns 8-13 and 18-25 of which are incorporated by reference herein for their description of branched multimer preparation. Additionally, U.S. Pat. No. 5,580,731, issued Dec. 3, 1996, is incorporated by reference herein for its description of N-4 modified pyrimidine nucleotides which can be used in the synthesis of the presently disclosed branched linking molecules.

Branched linking molecules can also be prepared in the form of dendrimeric oligonucleotides. See, for example, Shchepinov et al. (1997) *Nucleic Acids Research* 25(22): 4447-4454, wherein the authors describe the synthesis of a dendrimeric head on top of a conventional monomeric oligonucleotide utilizing a branched phosphoramidite with multiple protected primary hydroxyl groups. See also, Shchepinov et al. (1999) *Nucleic Acids Research* 27(15): 3035-3041, describing additional types of dendrimeric oligonucleotides and their preparation. These references are incorporated herein by reference for their description of dendrimeric oligonucleotides and preparation of same.

Additionally, branched linking molecules can be prepared using a combination of avidin/streptavidin and biotinylated nucleic acids. For example, an individual avidin/streptavidin molecule can be linked to four biotinylated nucleic acids via the avidin/streptavidin-biotin interaction. Linking molecules of this type can be prepared such that one of the four biotinylated nucleic acids comprises a nucleic acid sequence capable of specifically hybridizing to a distinct region of a nucleic acid target molecule of interest, while the remaining three biotinylated nucleic acids comprise nucleic acid sequences capable of hybridizing to nucleic acid molecules bound to a substrate as capture probes.

Nucleic acid linking molecules can also be prepared using chemical or enzymatic techniques such as conjugation, ligation and polymerization. These chemical or enzymatic techniques can be applied to form multiple sites in both linear and various branched formations.

In certain embodiments, one or more of the binding moieties of a linking molecule are designed to make use of specific, non-covalent binding interactions other than hybridization of complementary nucleic acids. Such interactions include, e.g., interactions between the following binding partners: biotin or biotin analogues/avidin or streptavidin, haptens/antibodies or antibody fragments, saccharides/lectins and specific ligands/receptors.

By way of example, FIGS. 11-15 illustrate synthesis schemes for various "branched" and "star" linking molecules comprising an oligodeoxynucleotide (ODN) (or analogue thereof) target-specific binding moiety and multiple capture probe-specific binding moieties comprising biotin or other non-covalent binding partner. While these Figures indicate the use of biotin as a binding moiety, such use is for illustrative purposes only, and it should be noted that any suitable non-covalent binding partner may be substituted. These linking molecules can be prepared via direct synthesis on an ODN (or analogue thereof) or through a two step synthesis process in which a branched or star moiety comprising biotin molecules or other non-covalent binding partner is prepared separately from a modified ODN (or analogue thereof) and the two components are subsequently conjugated to form a linking molecule comprising a target-specific binding moiety and multiple capture-probe specific binding moieties.

Figure 11:
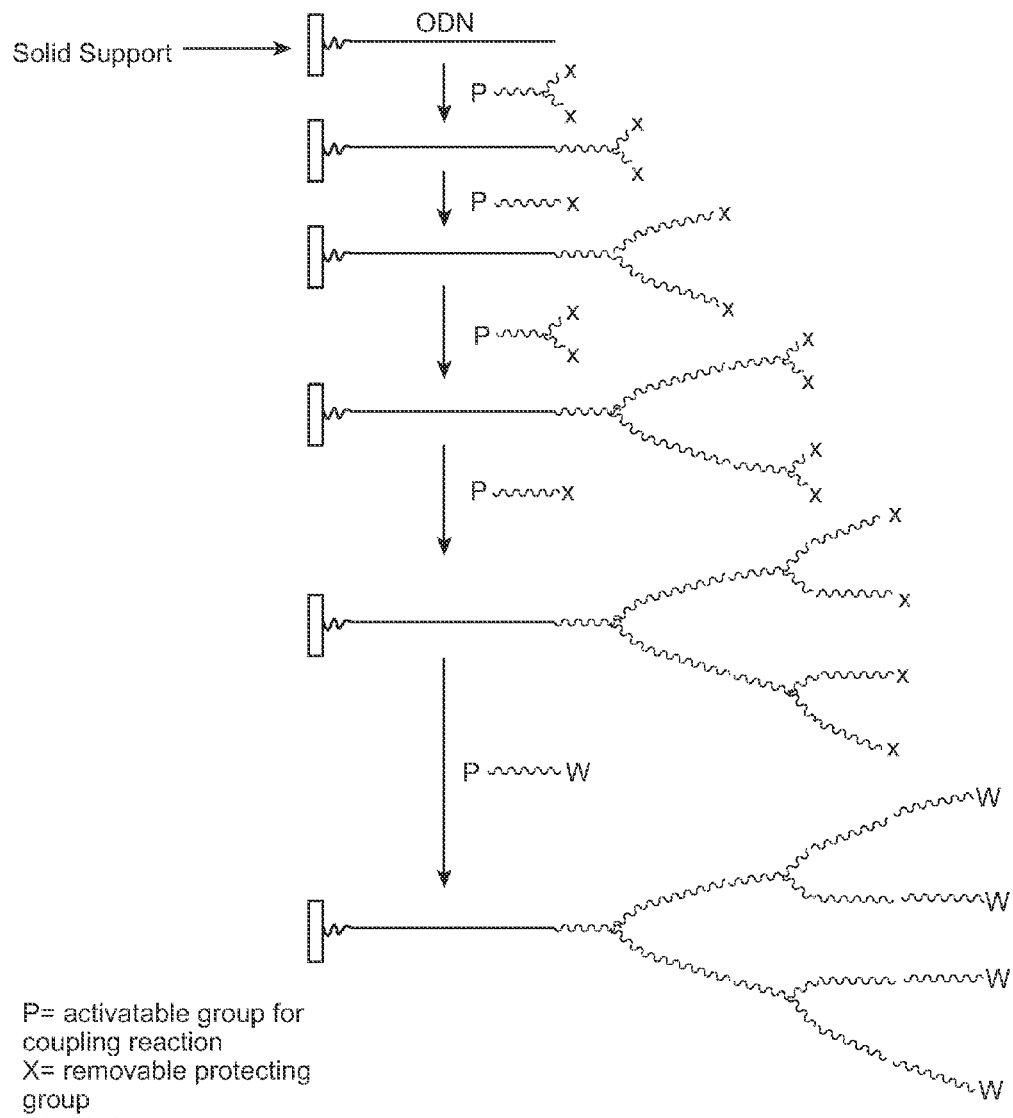
FIG. 11 illustrates a synthesis scheme for the direct synthesis of a branched linking molecule comprising multiple capture probe specific binding moieties.

FIG. 11 shows a direct synthesis scheme for the preparation of a branched linking molecule in which a branched moiety is synthesized directly onto an ODN bound to a solid support. The branched linking molecule can be synthesized via a variety known solid support or in situ synthesis methods.

Figure 12:
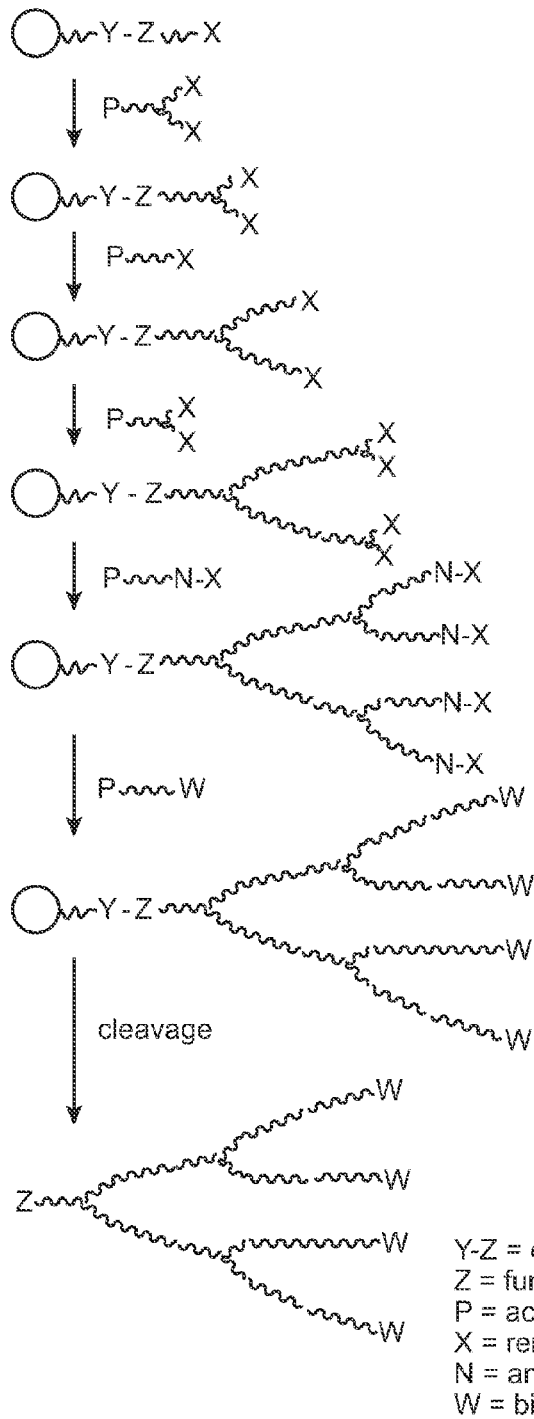
FIG. 12 illustrates a synthesis scheme for the synthesis of a branched moiety comprising multiple capture probe-specific binding moieties.
Figure 13:
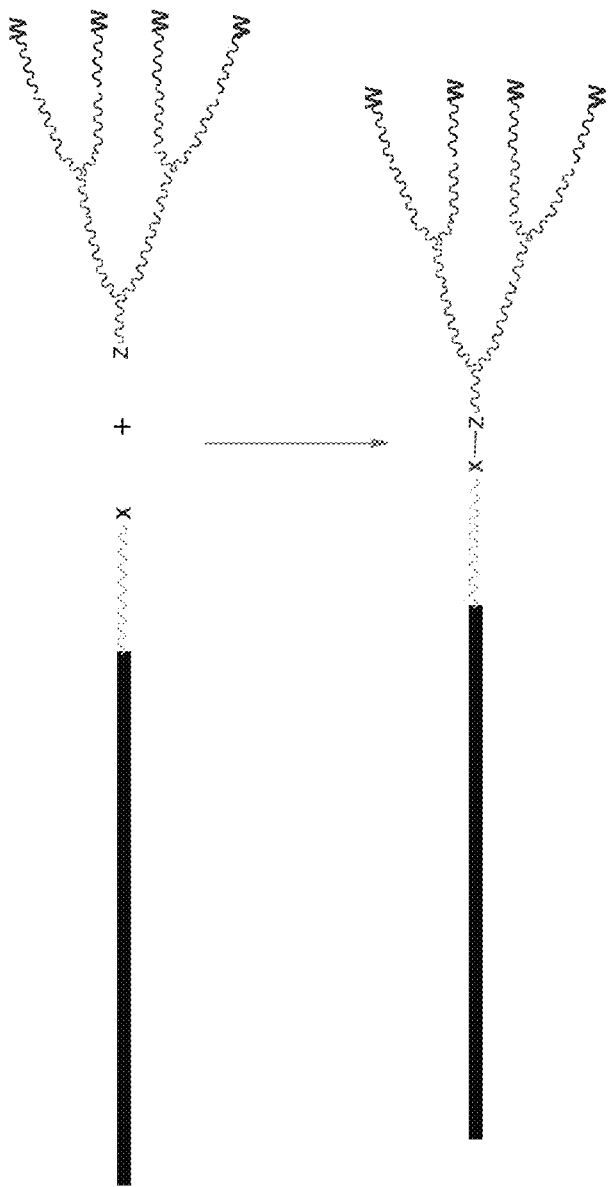
FIG. 13 illustrates a conjugation reaction between an ODN and a branched moiety to form a linking molecule comprising multiple capture probe-specific binding moieties.

FIG. 12 shows the synthesis of a branched moiety comprising multiple capture probe specific binding moieties. This branched moiety can then be conjugated to an ODN to form a linking molecule as illustrated in FIG. 13. A variety of functional groups and conjugation chemistries are available to facilitate this conjugation, e.g., click chemistry, Thio and maleimide, thio and bromo-alkyl, aldehyde and hydrazine or hydrazide, amine and NHS ester, disulfide bond formation, Diels-Alder Reaction, etc. The functional groups of these reactions are designated X and Z in FIG. 13.

Figure 14:
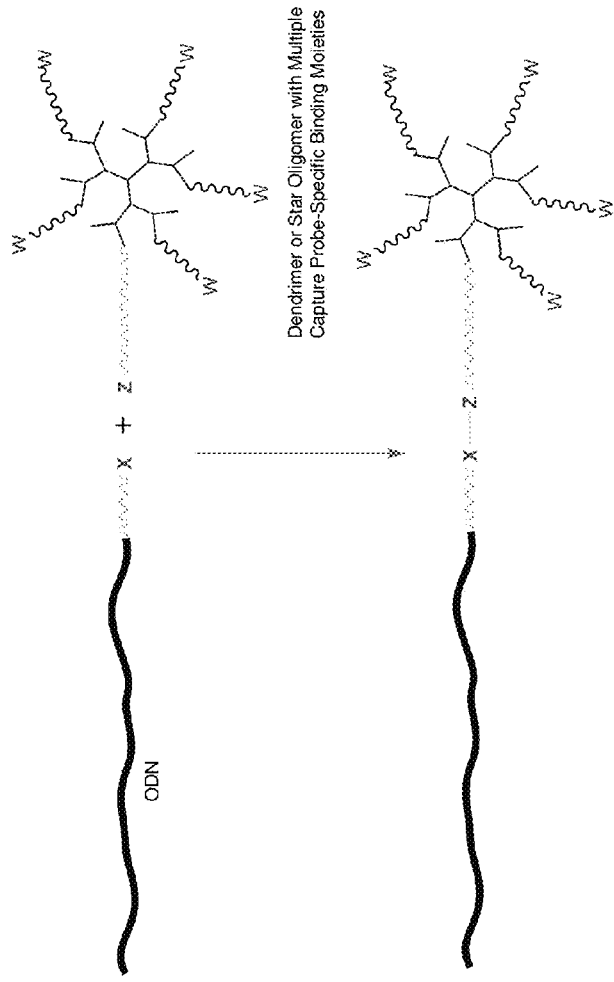
FIG. 14 illustrates the formation of a linking molecule by conjugation of ODN to dendrimer or star oligomer comprising multiple capture-probe specific binding moieties.
Figure 15:
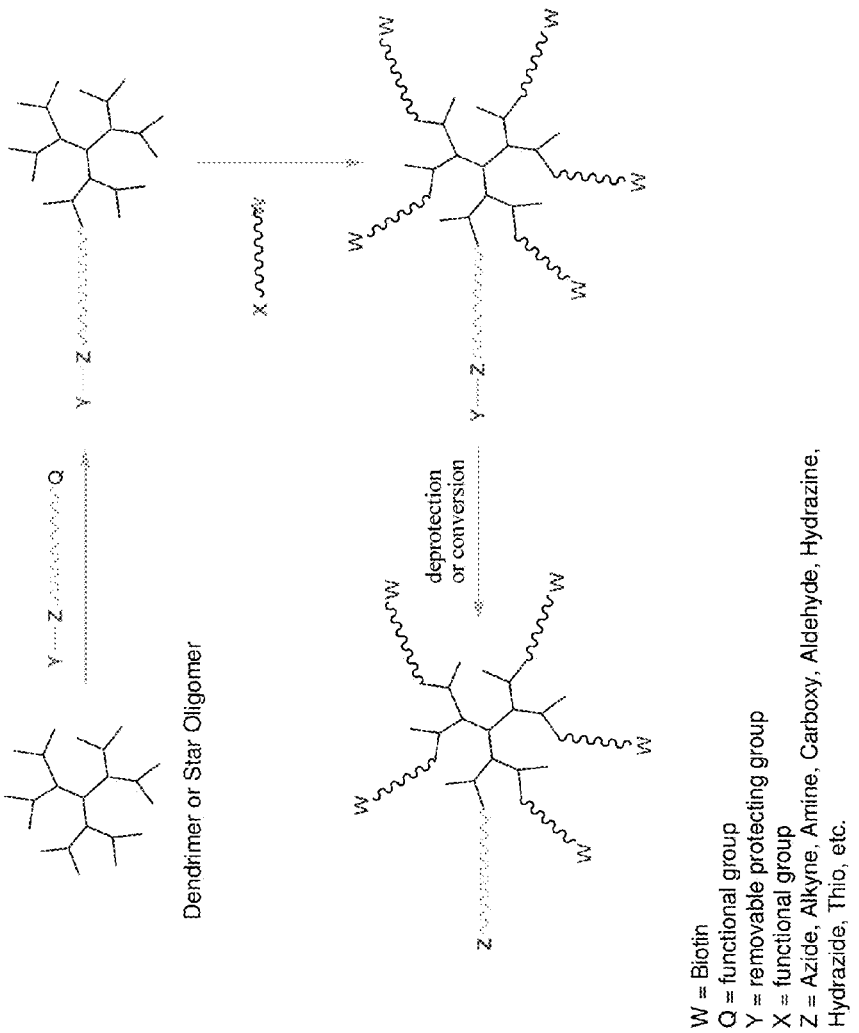
FIG. 15 illustrates the attachment of multiple capture probe-specific binding moieties and the introduction of a coupling linker on dendrimer or star oligomer.

Linking molecules can also be synthesized by conjugating modified ODN to dendrimer or star oligomers comprising multiple capture probe-specific binding moieties. FIGS. 14 and 15 together illustrate a two-step approach for the synthesis or modification of a dendrimer or star shape oligomer with multiple capture probe specific binding moieties followed by conjugation with a modified oligonucleotide. X and Z represent functional groups suitable for conjugation using, e.g., click chemistry, Thio and maleimide, thio and bromo-alkyl, aldehyde and hydrazine or hydrazide, amine and NHS ester, disulfide bond formation, Diels-Alder Reaction, etc.

Detectable Labels

There are a variety of detectable labels known in the art which can be utilized in connection with the disclosed methods and compositions. These include e.g, radioactive isotopes, fluorescers, chemiluminescers, chromophores, enzymes, enzyme substrates, enzyme cofactors, enzyme inhibitors, metal ions, magnetic particles, members of a specific binding pair and the like.

Detectable labels may be in the form of particles, e.g., microparticles or nanoparticles. Where a magnetic particle is utilized in the methods and/or compositions disclosed herein, the magnetic particle can be, e.g., a magnetic nano-particle or micro-particle. Magnetic particles include, for example, magnetic beads or other small objects made from a magnetic material such as a ferromagnetic material, a ferrimagnetic material, a paramagnetic material, or a superparamagnetic material. In some embodiments, the magnetic particles comprise iron oxide ($Fe_2O_3$ and/or $Fe_3O_4$) with diameters ranging from about 10 nanometers to about 100 micrometers. Magnetic nanoparticles are available, for example, from Miltenyi Biotec Corporation of Bergisch Gladbach, Germany. These are relatively small particles made from coated single-domain iron oxide particles, typically in the range of about 5 to about 500 nanometers diameter. Magnetic particles can also be made from magnetic nanoparticles embedded in a polymer matrix such as polystyrene. These are typically smooth and generally spherical having diameters of about 0.2 to about 5 micrometers. Particles of this type are available from Invitrogen Corporation, Carlsbad, Calif. Additional examples of magnetic particles include those described by Baselt et al. (1998) *Biosensors & Bioelectronics* 13: 731-739, Edelstein et al. (2000)*Biosensors & Bioelectronics* 14: 805-813, Miller et al. (2001) *J. of Magnetism and Magnetic Materials* 225: 138-144, Graham et al. (2002) *J. Appl. Phys.* 91: 7786-7788, Ferreira et al. (2003) *J. Appl. Phys.* 93, pp. 7281-7286, and U.S. Patent Application Publication No. 2005/0100930 (published May 12, 2005).

In one aspect, magnetic particles having an average diameter of about 10 nanometers to about 1000 nanometers are utilized in the disclosed methods and compositions, e.g., magnetic particles having an average diameter of about 100 nm to about 900 nm, about 200 nm to about 800 nm, about 300 nm to about 700 nm, about 400 nm to about 600 nm, or about 500 nm.

Cross-Linking to Strengthen and/or Stabilize a Binding Complex

The strength and/or stability of a binding complex can be increased by cross-linking and through the introduction of high-strength covalent bonds. These techniques can be utilized in combination with the linking molecules described herein to provide strong, stable target molecule-substrate binding complexes.

For example, a binding interaction between two or more of the binding entities found in a single target molecule-substrate binding complex can be strengthened and/or stabilized by the introduction of one or more cross-linking agents. This type of cross-linking can be described as "intra-complex cross-linking." In some embodiments, this "intra-complex cross-linking" involves the introduction of covalent bonds into an intramolecular complex. It may be desirable, for example, to stabilize a target bound to a biochip surface via one or more linking molecules prior to contacting with a substrate comprising a detectable label. In some embodiments, it may be desirable to further stabilize the binding complex after a detectable label has bound to the target molecule via one or more linking molecules.

The disclosure also contemplates the use of cross-linking agents to introduce "inter-complex cross-linking." For example, in one embodiment a single complex can be described by the following formula A-B-C-D, wherein A=a biochip surface comprising a plurality of target-immobilization probes, B=a target molecule, C=one or more linking molecules, and D=a detectable label comprising a plurality of captures probes bound thereto. This single complex can be linked to one or more additional complexes present on a substrate surface through the introduction of cross-linking agents.

Cross-Linking Through the Introduction of Covalent Bonds

Cross-linking agents can be introduced to facilitate the formation of covalent bonds between members of a binding complex and/or between complexes. Covalent bonds are usually in the range of 300-400 kJ/mol. These bonds are many folds stronger than the non-covalent binding interaction between a receptor and its ligand, protein and protein or hybridized double stranded nucleic acids.

Figure 7:
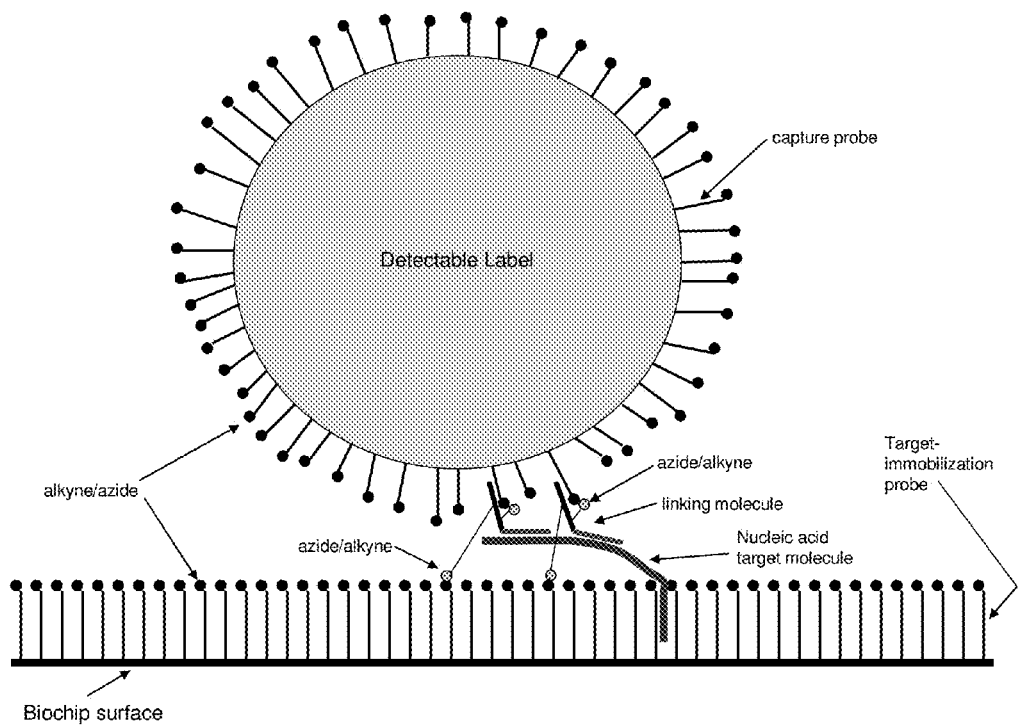
FIG. 7 illustrates the use of alkyne/azide functional groups as cross-linking agents to introduce covalent bonds into a complex comprising a biochip surface, a target-immobilization probe, a plurality of linking molecules and a detectable label.
Figure 8:
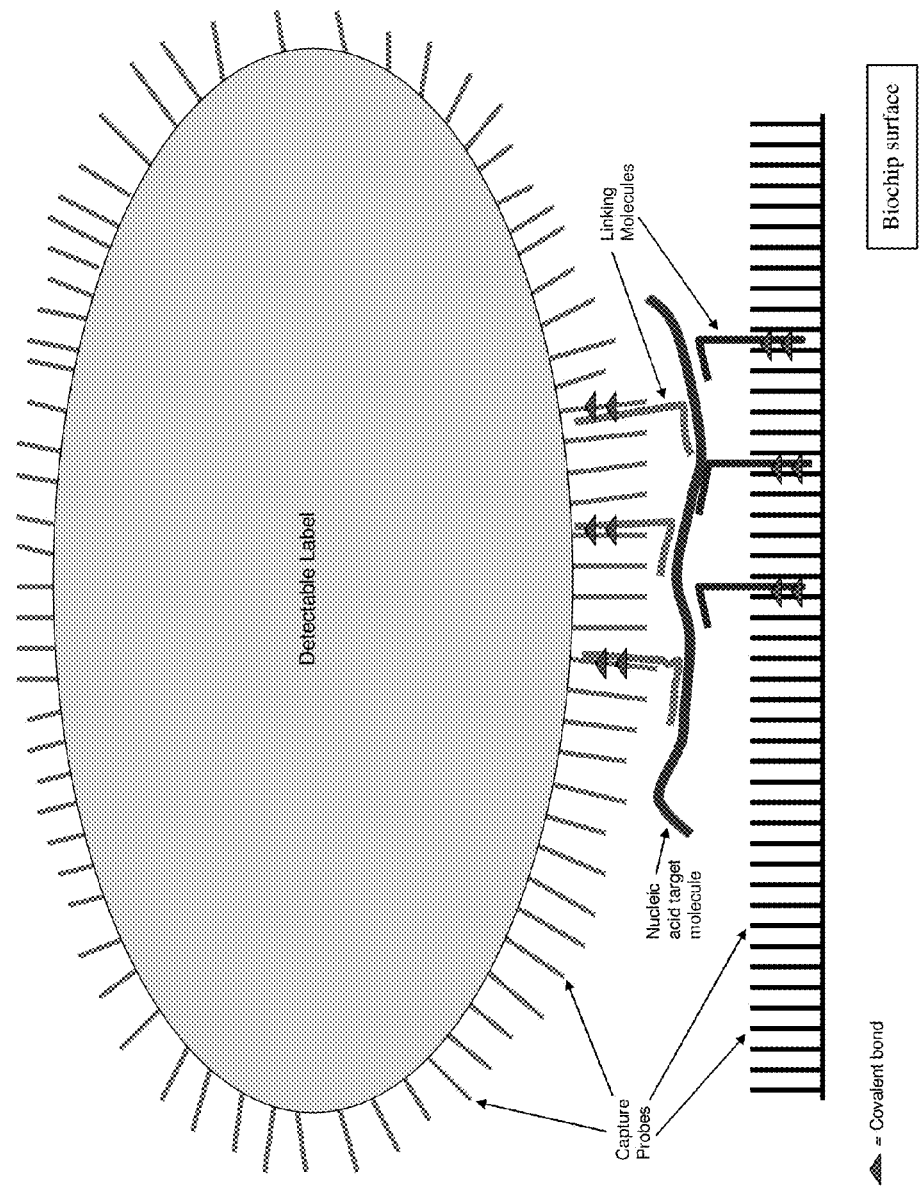
FIG. 8 illustrates the use of cross-linking agents to introduce covalent bonds into a complex comprising a biochip surface, a first plurality of linking molecules, a nucleic acid target molecule, a second plurality of linking molecules, and a detectable label.

FIGS. 7 and 8 show exemplary embodiments involving the use of cross-linking agents to introduce covalent bonds. FIG. 7 illustrates an embodiment wherein the cross-linking agents comprise a first member of a specific binding pair (e.g., azide/alkyne) and a second member of a specific binding pair (e.g., alkyne/azide), and wherein the first member of the specific binding pair forms a covalent bond when reacted under suitable conditions with the second member of the specific binding pair. In FIG. 7 both the target-immobilization probes on the biochip surface and the capture probes on the detectable label separately comprise a first member of a specific binding pair (e.g., alkyne/azide). The second members of the specific binding pair (e.g., azide/alkyne) are shown conjugated to the capture probe-specific binding moieties of the linking molecules bound to the nucleic acid target molecule. Under suitable conditions, first and second members of the specific binding pair will react to form one or more covalent bonds which strengthen and stabilize the binding complex comprising the biochip surface, target-immobilization probe, linking molecules and detectable label. While FIG. 7 demonstrates cross-linking with respect to a particular linking molecule embodiment, it is to be understood that such cross-linking may be applied to complexes comprising any of the linking molecule embodiments disclosed herein.

A variety of covalent bond forming binding pair interactions are known in the art including Cu-catalyzed azide/alkyne [3+2] cycloaddition "click chemistry," azide/DIFO (Difluorinated Cyclooctyne) Cu-free click chemistry, azide/phosphine "Staudinger Reaction," azide/triarylphosphine "Modified Staudinger Reaction," and catalyzed olefin cross metathesis reactions. These binding pair reactions may be utilized to introduce covalent bonds to stabilize and/or strengthen the interactions between members of a (target)-(linking molecule)-(substrate) binding complex. Those of skill in the art will understand that some of these reactions, e.g., Cu-catalyzed azide/alkyne [3+2] cycloaddition, require the addition of a catalyst agent to catalyze the binding pair interaction, while other such as the azide/DIFO reaction do not.

FIG. 8 illustrates an exemplary embodiment in which the introduction of cross-linking agents results in the formation of covalent bonds between hybridized nucleic acid strands. FIG. 8 shows covalent bond formation between capture probes bound to a biochip surface and linking molecules bound to a nucleic acid target molecule. FIG. 8 also shows covalent bond formation between capture probes bound to the surface of a detectable label and linking molecules bound to the nucleic acid target molecule.

There are a variety of agents available in the art which can be used to crosslink between strands of hybridized nucleic acids, between nucleic acids and proteins, and between different protein molecules. Cross-linking agents of different lengths and combinations of functional groups are available commercially.

For example, psoralens, a class of photo mutagenic compounds that form covalent nucleic acid adducts through photochemical addition, can be utilized. The primary reaction is cyclobutane ring formation between the 5,6 double bond of thymidine in DNA and either the 4',5' or 3,4 double bond of the psoralen. Reaction at the 4',5' double bond creates a furan-side monoadduct, which can further react at a site with a flanking pyrimidine on the opposite strand to create an interstrand cross-link. Spielmann et al. (1995) *Proc. Natl. Acad. Sci.* USA Vol. 92, pp. 2345-2349. See also, Okamoto et al. (2001) Org. Lett. March 22; 3(6):925-7, describing the synthesis of a psoralen containing peptide nucleic acid (PNA) from 8-methoxypsoralen. PNA containing a psoralen unit at strand end forms a stable duplex with complementary DNA. Psoralen's with additional functionality have also been synthesized. For example, Saffran et al. (1988) *Nucleic Acids Research;* 16(15):7221-31, describe the synthesis of a biotinylated psoralen (BPsor). BPsor photoreacts with DNA to form interstrand cross-links while providing an additional binding functionality in the form of the attached biotin which can then interact with a streptavidin molecule.

Crosslinking of hybridized nucleic acid molecules can also be accomplished as described in U.S. Pat. No. 6,800,768 (issued Oct. 5, 2004), wherein non-nucleosidic photoactive coumarin derivatives are incorporated into nucleic acids to facilitate crosslinking.

Alternatively, cross-linking agents can be designed and synthesized to fit the requirements of a particular cross-linking situation.

As described in Pendergrast et al. (1992) *Proc. Natl. Acad. Sci.* USA Vol. 89, pp. 10287-10291, photocrosslinking can also be utilized to stabilize binding interactions between proteins and nucleic acids. Specifically, Pedergrast et al. incorporate a photoactivatable crosslinking agent at a single amino acid within a protein by a two-step procedure consisting of site-directed mutagenesis followed by cysteine-specific chemical modification. First, site-directed mutagenesis is used to introduce a unique solvent accessible cysteine residue at the position of interest. Then, one derivatizes the resulting protein with a cysteine specific heterobifunctional photoactivatable crosslinking agent, e.g., 4-azidophenacyl bromide. Under defined conditions, reaction of 4-azidophenacylbromide with a protein having a unique solvent-accessible cysteine residue results in complete and highly selective derivatization of the cysteine residue to yield a conjugate of the form [(4-azidophenacyl)-Cys]protein. One then forms the protein-DNA complex and UV irradiates the protein-DNA complex to introduce crosslinking.

The crosslinking agents can be applied as separate and independent reagents. Alternatively, cross linking functional groups can be directly conjugated to the linking molecules, capture probes, target immobilization probes, substrates, etc. The functional group can be activated on command by input such as light, pH changes or specific chemicals applied at a desired point in time. Additionally, the binding moieties and/or linking molecules disclosed herein can be designed to make them suitable for the application of crosslinking agents of choice. For example, conjugating protein or other chemical entities to target-specific binding moieties comprising nucleic acids makes it possible to broaden the selection of cross linking agents to those originally not applicable for nucleic acids.

Introduction of Complementary Nucleic Acids

Complementary nucleic acid sequences can be introduced to enhance the strength of binding between binding complexes. For example, a molecule comprising regions of nucleic acid complementarity to the linking molecules of two or more binding complexes described herein can be utilized to produce inter-complex cross-linking. Such nucleic acids can be designed to be of appropriate length to ensure proper hybridization. This can be achieved by inserting a linker section of desired length in the bridging nucleic acid. The linker section can comprise any suitable substance including nucleotides and other polymers such as polyethylene glycol.
Methods of Creating a Target Molecule Substrate Complex Having Multiple Intra-Complex Binding Interaction Sites The linking molecules described herein find use in methods designed to create a target-substrate complex having multiple intra-complex binding interaction sites. These methods can be used, for example, in connection with assays designed to determine the presence or absence of a particular target molecule in a sample. The disclosed methods can also be used to determine quantitatively the amount of a particular target molecule in a particular sample. Generally, the methods described herein involve combining in a reaction mixture a sample suspected of containing a target molecule, one or more capture probe functionalized substrates and one or more linking molecules as described herein.

In one embodiment, the method utilizes two distinct types of substrates. The first type comprises a biochip surface, and the second type is a detectable label or is modified to include a detectable label. A sample suspected of containing a target molecule is combined in a reaction mixture with one or more linking molecules described herein. After allowing a sufficient amount of time for the linking molecules to bind to the target molecule if present, the reaction mixture is contacted with a substrate comprising a biochip surface as described herein. The biochip surface can be functionalized with one or more target immobilization probes. Where target immobilization probes are utilized, the (target molecule)-(linking molecule) complex, can be directly bound by the target immobilization probes. The reaction mixture is then contacted with the second type of substrate, i.e., the detectable label. Capture probes present on the detectable label allow for binding to the one or more linking molecules bound to the target molecule. In this manner, an immobilized complex comprising the target molecule and the detectable label is formed, wherein the complex comprises multiple binding interaction sites. The presence and/or quantity of the detectable label can then be detected according to a variety of methods known in the art, e.g., through the use of a magnetic sensor incorporated into a biochip.

In some embodiments, one or more of the above binding steps are followed by one or more wash steps to remove non-specifically bound molecules.

It should be noted that although some embodiments utilize a target immobilization probe to immobilize the target molecule on the biochip surface, immobilization of the target molecule on the biochip surface can also be accomplished using one or more linking molecules in combination with one or more capture probes bound to the biochip surface. As such, in some embodiments the disclosed methods result in the formation of a binding complex, wherein a target molecule is bound to a biochip surface via linking molecules which bind to capture probes on the biochip surface, and wherein a detectable label is bound to the target molecule via linking molecules which bind to capture probes on a detectable label.

Kits

Also provided by the present disclosure are kits for use in practicing the methods disclose herein. The kits typically include one or more linking molecules, as described above. In addition, the subject kits can further include one or more detectable labels, as described above, e.g., one or more magnetic particles comprising a plurality of capture probes. The subject kits can also include a substrate comprising a biochip surface, as described above. Furthermore, the kits may include one or more positive or negative controls. The kits can also include one or more cross-linking agents, as described herein.

The various components of the kit may be present in separate containers or certain compatible components may be precombined into a single container, as desired.

In addition to the above components, the kits can further include instructions for practicing the methods described herein. These instructions may be present in the kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); and the like.

Example 1

Improved Labeling of Substrate Immobilized Oligos with Magnetic Beads Through the Use of Multiple Non-Covalent Binding Interactions In order to demonstrate improved labeling of substrate immobilized nucleic acids through the use of multiple non-covalent binding interactions, immobilized oligo complexes comprising 0, 1 or 2 biotin labels were compared based on their performance in anchoring magnetic beads of different sizes.

Materials and Methods

Two different oligo-functionalized substrates were prepared as follows. A first set of oligonucleotide probes of the same nucleic acid sequence was conjugated to a first substrate surface and a second set of oligonucleotide probes having the same nucleic acid sequence as the first set was conjugated to a second substrate surface. The oligonucleotide probes had sulfhydryl groups on their 5' ends and were conjugated separately to the two substrate surfaces through maleimide groups on the substrate surfaces. For the first substrate, the oligonucleotide probes were labeled with a biotin molecule at the distal end of the probe relative to the substrate surface (designated 010 in FIGS. 9 and 10). For the second substrate, the oligonucleotide probes were unlabeled (designated 001 in FIGS. 9 and 10).

Four experimental substrates were prepared by applying two different sets of oligonucleotides to each of the oligo-functionalized substrate surfaces under hybridization conditions. The oligonucleotides applied to the surfaces were of the same sequence and were complementary to the sequence of the immobilized oligonucleotides on the substrate surfaces. The first of the two different oligonucleotide sets was labeled with biotin molecules such that when an applied oligonucleotide of the set was hybridized to an immobilized oligonucleotide on the substrate surface, the biotin molecule was located at the distal end of the applied oligonucleotide relative to the substrate surface (designated 008 in FIGS. 9 and 10). The second of the two different oligonucleotide sets was unlabeled (designated 025 in FIGS. 9 and 10). In this manner, four parallel experimental substrates were conducted as shown in each of FIGS. 9 and 10. For each of the four experimental substrates, three parallel experiments were performed by applying one of three different sizes of streptavidin coated paramagnetic beads (A=0.3 μm diameter, B=0.5 μm diameter, and C=1.0 μm diameter). Each of the experimental substrates was subjected to approximately 5-10 wash steps to remove unbound beads. The substrates were then imaged under both low and high magnification in order to make a qualitative determination as to the number of bound beads.

Results

Figure 9:
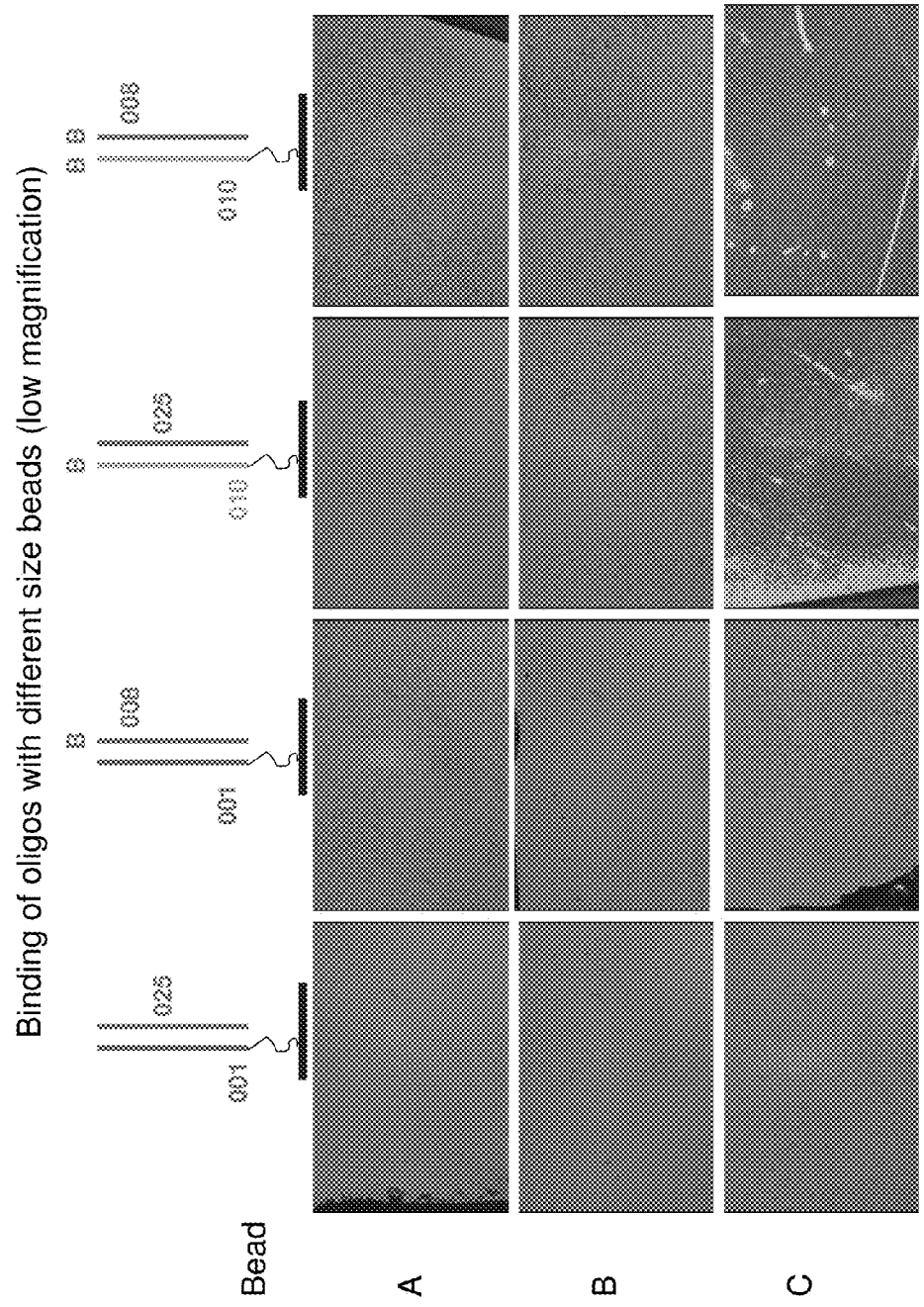
FIG. 9 shows the results of magnetic bead labeling of immobilized oligonucleotides having multiple non-covalent binding sites for magnetic beads. Images are shown at low magnification.
Figure 10:
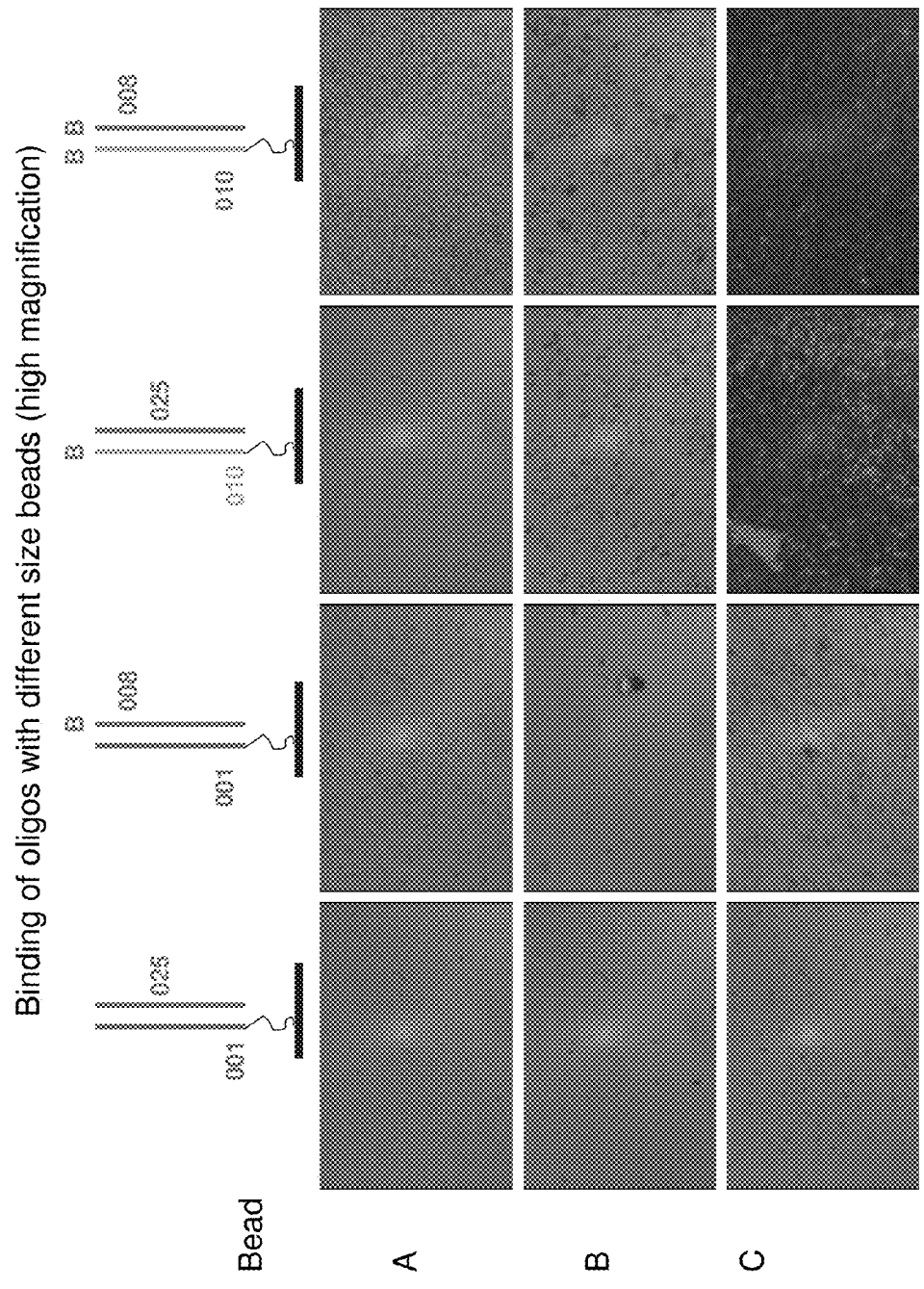
FIG. 10 shows the results of magnetic bead labeling of immobilized oligonucleotides having multiple non-covalent binding sites for magnetic beads. Images are shown at high magnification.

FIGS. 9 and 10 show images of the various substrates under low and high magnification respectively. As shown in these images, increasing the number of non-covalent binding interaction sites between the bead and the hybridized DNA complex by increasing the number of biotin-streptavidin binding interactions visually increased the number of magnetic beads bound via the hybridized DNA complex to the substrate surface. This increase in bead binding would increase the detection sensitivity when using the beads as detectable labels for a nucleic acid target of interest.

Example 2

Formation of a Target-Substrate Complex Utilizing Nucleic Acid Linking Molecules A Prophetic example utilizing methods and compositions disclosed herein is described below. A segment of human immunodeficiency virus (HIV) sequence is cloned and transcribed into RNA as a model nucleic acid target molecule. Alternatively single stranded DNA is formed by applying single stranded exonuclease to digest the PCR product of DNA reverse transcribed from the HIV sequence as a model nucleic acid target molecule. Nucleic acid linking molecules capable of specifically binding to different regions of the nucleic acid target molecule are then prepared. Each of the nucleic acid linking molecules is also designed to include a nucleic acid sequence common to each of the linking molecules. This "capture probe-specific binding moiety" of the linking molecules is designed such that it is capable of hybridizing to a nucleic acid sequence ("capture probe") bound to the surface of a magnetic particle. This configuration is illustrated graphically in FIG. 6B. The common capture probe-specific binding moieties are designed to minimize intramolecular hybridization and achieve maximal open structure for the linking molecules.

The nucleic acid linking molecules are designed using commercially available software, e.g., Primer Express available from Applied Biosystems or Vector NTI available from Invitrogen. To design the nucleic acid linking molecules, one computes, designs and verifies through reiterations a sequence that has the least amount of secondary structure. Particular care is taken to minimize hair pin structures and internal secondary structure. This makes the linking molecule more open and accessible for hybridization with both the target molecule and the nucleic acid sequences bound on the surface of the magnetic particle. In order to achieve highly stable hybridized structure with the target molecule and the nucleic acid "capture probes," linking molecule and target sequence regions are preferably selected which have regions of high G, C content. The nucleic acid linking molecule sequences are also selected such that they display minimal binding free energy with respect to each other so that binding between linking molecules will not interfere with target the binding capability of the linking molecules.

Initially, a sample containing the HIV nucleic acid target molecule is incubated with two sets of linkers L1 and L2 under conditions suitable for the linkers to bind to the target molecules. Each member of each set has a segment with sequence complementary to a different region of the target molecule and a second segment that binds to either a capture probe functionalized on the biochip surface or a capture probe functionalized on the detectable label particles. Afterwards, the target molecules bound with linking molecules are applied to the biochip surface. A wash step designed to remove non-specifically bound linking molecules is then performed. In a final hybridization step, the reaction mixture is contacted with paramagnetic beads functionalized with nucleic acid capture probes capable of binding the common capture probe-specific binding moieties of the linking molecules. A final wash step is conducted to remove paramagnetic beads not specifically bound to the (linking molecule)-(target nucleic acid)-(target immobilization probe) binding complexes.

The presence and/or amount of immobilized paramagnetic beads is then detected using a Magnetic Tunnel Junction (MTJ) sensor incorporated into the biochip.

Example 3

Synthesis of Multiple Capture Probe-Specific Binding Moieties on a Branched Molecule and Conjugation with Oligo-Deoxynucleotide (ODN) as Target Binding Moiety and Optionally with Reactive Groups for Forming Covalent Bonds with the Substrate As indicated above, FIGS. 11-15 illustrate synthesis schemes for various "branched" and "star" linking molecules comprising an oligodeoxynucleotide (ODN) target-specific binding moiety and multiple capture probe-specific binding moieties. With minor modification, the synthesis can be performed to generate reactive groups to conjugate with nucleic acids, biotin, polypeptide tags, receptors or other agents with specific binding affinity for capture probes. (Optionally, in addition to the multiple capture probe specific binding moieties, one or more reactive groups can be introduced to provide for covalent bond formation to further strengthen a binding complex comprising the linking molecule.)

Two exemplary synthesis approaches are described in the following prophetic example. Both approaches employ solid phase oligonucleotide synthesis chemistry schemes with variations such as applying monomers for solid surface synthesis of different sizes and functional groups to produce the desired spacing and chemistry. One approach is to synthesize the oligonucleotide sequence for binding to the nucleic acid target and the branched moiety for binding the capture probes as a whole on the solid support as depicted in FIG. 11. Alternatively, the branched moieties and the target binding moieties are synthesized separately and then conjugated to form the whole molecule afterwards as depicted in FIGS. 12 and 13.

In both approaches, controlled pore glass (CPG) with a cleavable protecting group DMT (dimethoxytrityl) on solid support is used to start the solid phase synthesis. After removing the DMT group with acid solution, if the approach is to directly synthesize the entire linking molecule, oligonucleic acid synthesis is performed first to generate a stretch of target binding oligonucleotide before starting the synthesis of the branched moieties as depicted in FIG. 11. If the approach is to synthesize the two parts separately and then conjugate them together, as depicted in FIGS. 12 and 13, the synthesis of the branched moiety on the solid surface can start right away on the solid support.

A unit of "Y" shaped bifunctional linker is coupled onto the solid support using phosphoramidite synthesis chemistry. As depicted in FIG. 12 the "Y" shaped bifunctional linker has at the ends of its two symmetrical arms, two functional groups capped by protecting groups X, such as DMT. The DMT groups can be deblocked using acidic solution, and then another unit of the "Y" shaped bifunctional linker can be incorporated. After a desired number of units of "Y" shaped bifunctional linker are incorporated into the backbone, The DMT groups can be deblocked using acidic solution, and standard oligonucleotide synthesis techniques can be performed to form stretches of oligonucleotide at the end of each of the arms of the linker, wherein the stretches of oligonucleotide have sequences complementary to capture probes on a substrate. For capture probe binding groups other than oligonucleotides, after the removal of the protection group such as DMT, the exposed hydroxyl groups can be modified with a linker containing biotin group or converted to other groups such as amino or thio groups for further conjugation with polypeptides or other entities of choice. At the completion of the synthesis, the whole branched linker molecule can be cleaved from the CPG solid support using a strong alkaline solution. The final compound can be used to produce complexes comprising target molecules and detectable magnetic particles on a MTJ biosensor.

Example 4

Synthesis of Multiple Capture Probe-Specific Binding Moieties on a Dendrimer Molecule and Conjugation with Oligo-Deoxynucleotide (ODN) as Target Binding Moiety A prophetic example of a linking molecule synthesis scheme utilizing dendrimers is as follows:

Polyamidoamine (PAMAM) dendrimers of various generations (sizes) with a cystamine core and terminal amino groups on the dendrions are commercially available from Dendritic Nanotechnologies Inc. (Dendritic Nanotechnologies, Inc., 2625 Denison Drive. Mount Pleasant, Mich. 48858). The terminal amino groups can be readily derivatized to form other functional groups and be cross-linked to proteins and peptides such as antibodies and various tags, nucleic acids or reactive groups by using various modification or cross linking reagents which are available commercially from Sigma-Aldrich or Pierce Biotechnology in Thermo Fisher Scientific.

Either before or after the modification of the terminal amino groups, which results in the formation of multiple capture probe-specific binding moieties, the dendrimers with cystamine core can be reduced to sulfhydryl groups which provide a unique site to allow the conjugation of various target-specific binding moieties. Conjugation of the functionalized dendritic molecule with a free sulfhydryl group to a nucleic acid target-specific binding moiety usually requires the use of a heterobifunctional cross linker such as succinimidyl 4-[N-maleimidomethyl]cyclohexane-1-carboxylate. Optionally the conjugation can be mediated through a spacer to provide adequate spacing and minimize steric hindrance.

In this way, a linking molecule comprising a target-specific binding moiety and multiple capture probe-specific binding moieties can be synthesized.

Example 5

"Two-Step" Synthesis Scheme for a Branched Linking Molecule

In order to synthesize a branched linking molecule the following prophetic synthesis scheme utilizing phosphoramidite chemistry on a solid support can be performed.

Figure 16:
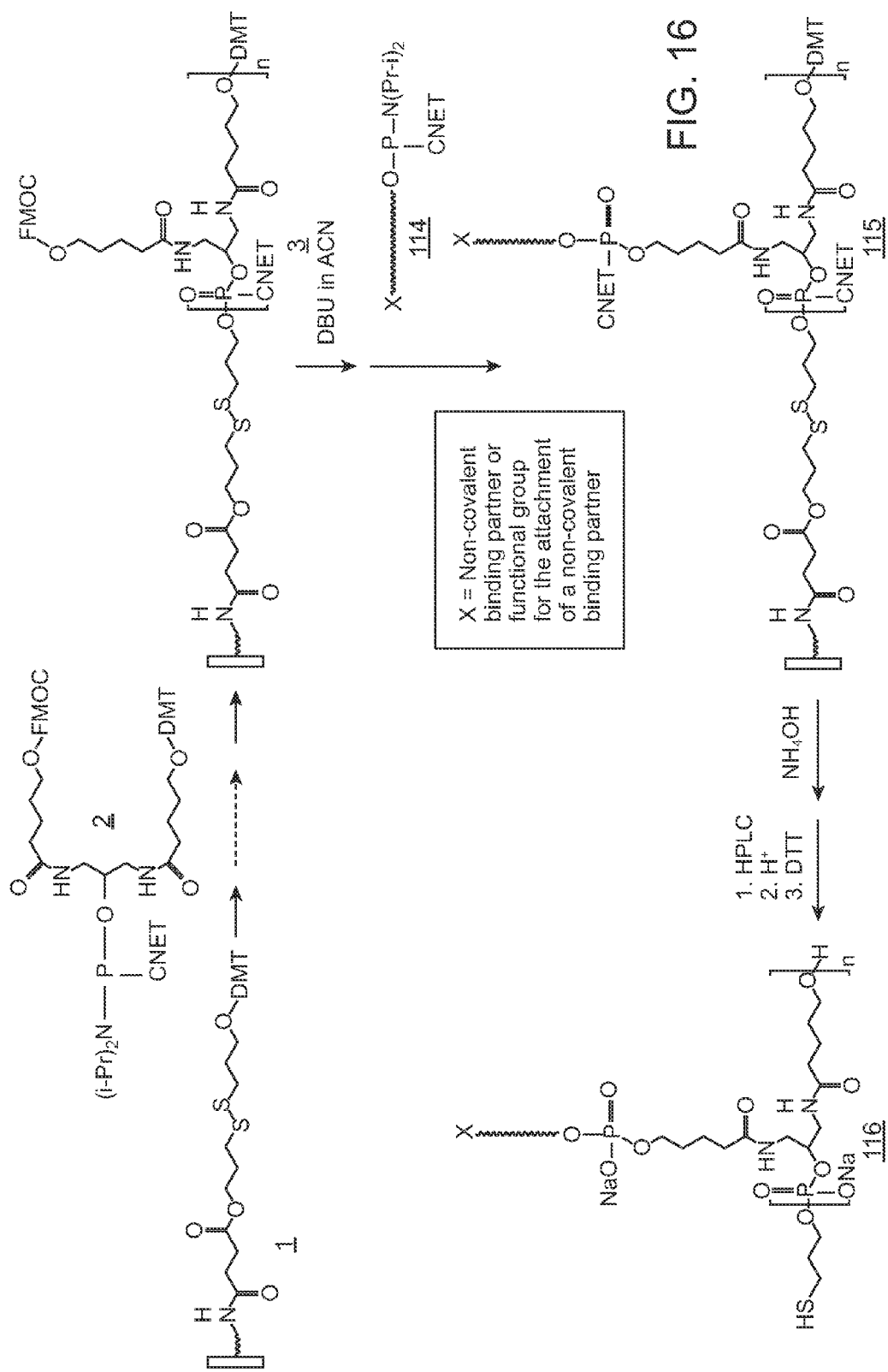
FIG. 16 illustrates a synthesis scheme using phosphoramidite chemistry with various monomers X for the synthesis of a branched moiety comprising multiple first members of a non-covalent binding pair.

As indicated in FIG. 16, controlled pore glasses beads (CPG) derivatized with a cleavable monomer (1), are used as solid support to start the synthesis. After removing the protecting group DMT (dimethoxytrityl) with acid solution a hydroxyl group is exposed. A unit of "Y" shaped bifunctional monomer (2) is coupled to monomer (1) using phosphoramidite chemistry. The "Y" shaped bifunctional monomer (2), called asymmetric doubler phosphoramidite, has two different protecting groups at each terminal: DMT, an acid labile group, and FMOC, a base labile group. The DMT group can be removed again using acidic solution, and then another unit of the "Y" shaped bifunctional monomer (2) is incorporated to extend the backbone of the branched entity.

Multiple units of the "Y" shaped bifunctional monomers can be incorporated by repeating the same phosphoramidite chemistry. The FMOC protecting groups are stable during the multiple iterations of the coupling reactions. After the desired number of units of "Y" shape bifunctional monomer is incorporated into the backbone, the FMOC protecting group can be removed using a weak alkaline solution, e.g., 1,8-diazabicyclo[5,4,0]undec-7-ene (DBU) in acetonitrile, to expose the hydroxyl groups on the termini of the branches. Various functional groups X can be introduced onto the hydroxyl groups using different phosphoramidite modifiers (114). For example, the functional groups X can be: biotin or any other suitable non-covalent binding partner.

Some functional groups introduced on the side chains of the branched entities, such as amine, hydrazide aldehyde, carboxylate, etc. can be used for conjugation with biomolecules, such as oligonucleotides (e.g., DNA or RNA), peptide, protein, carbohydrate, lipid, etc.

After the attachment of the phosphoramidite modifiers with the functional groups, the CPG solid support bearing the branched entity (115) can be treated with concentrated ammonium hydroxide to remove the protecting groups and cleave the branched entity from the solid support. The desired full length branched product containing a trityl hydrophobic group can be isolated from the crude mixture using HPLC (High performance Liquid Chromatography). Afterwards, trityl group is removed by treating the purified product with acid. The disulfide bond can be reduced using a reducing reagent, such as DTT, to generate a thio group at the terminus of the branched linker (116). The branched linker (116) can be used for conjugation with biomolecules with affinity for the target molecules, e.g., oligonucleotides.

Figure 17:
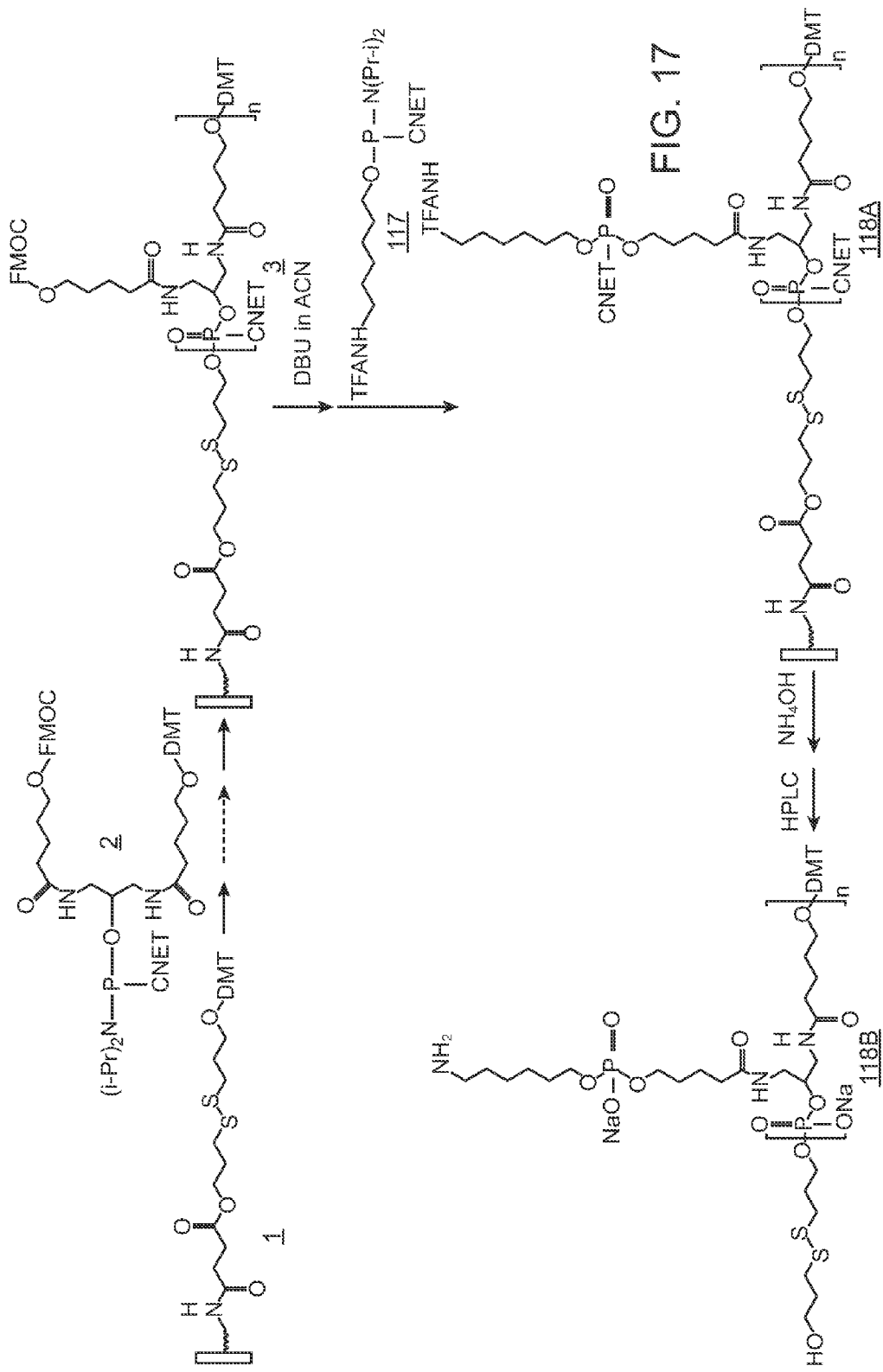
FIG. 17 illustrates a synthesis scheme for a branched moiety comprising multiple amino groups which can be converted to various first members of a non-covalent binding pair.

A method for introducing amino functional groups onto the side chains of the branched entities for conjugating with various biomolecules is shown in FIG. 17.

Using the phosphoramidite synthesis chemistry described above, one can incorporate a chosen number of units of "Y" shape bifunctional monomer (2) to form the branched entities (3) on the solid support. The FMOC protecting group can be removed with a weak alkaline solution, e.g., DBU in acetonitrile. On the exposed hydroxyl group, an amino modifier phosphoramidite monomer, such as 5'-Amino-Modifier C6-TFA (117) (from Glen research) can be coupled to produce molecule (118A). Then, the branched entity can be deprotected and cleaved from the solid support by treating it with concentrated ammonium hydroxide.

Figure 18:
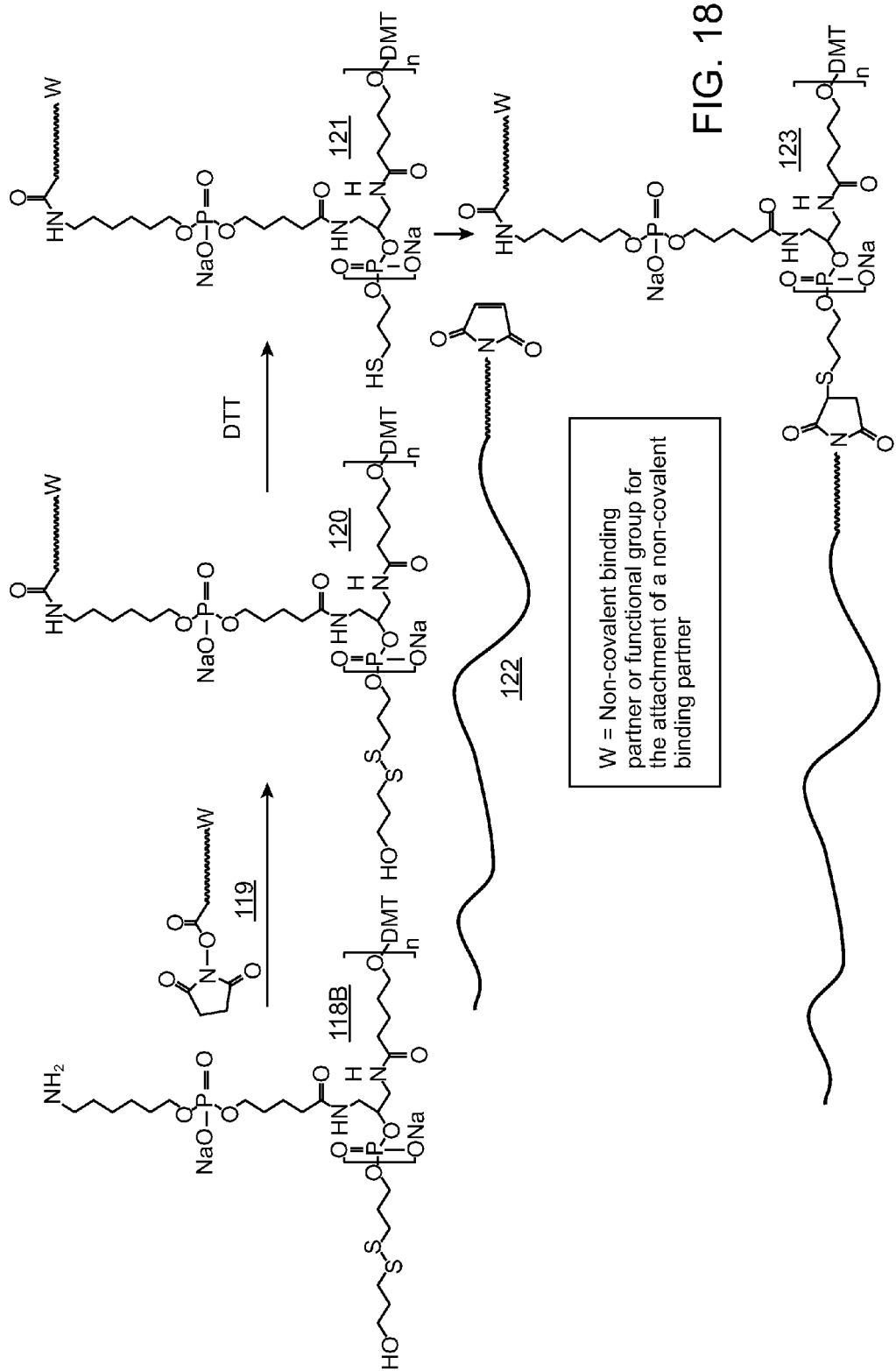
FIG. 18 illustrates a synthesis scheme using the branched moiety comprising multiple amino groups shown in FIG. 17 for the synthesis of a branched moiety comprising multiple first members of a non-covalent binding pair and its conjugation with a target-specific binding moiety.

After HPLC purification, the branched entity with amino groups on its side chains (118B) is ready for further conjugation. Many modification and cross linking reagents can be used. As shown in FIG. 18, a linking reagent (119) with N-hydroxysuccimide (NHS) ester at one terminus and a non-covalent binding partner (W), at the other terminus can be utilized. Linkers like (119) are available commercially or can be custom synthesized. Many biomolecules, such as carbohydrate, peptide, protein, DNA RNA, etc, can be chemically modified or conjugated with linkers to introduce the NHS ester group for reacting with the amino groups on the branched entity (118B).

After the formation of (120) by modifying the side chains of (118B) with (119), the disulfide bond in (120) can be converted to a free thio group in (121) by applying reduction reagent like DTT. Then, a maleimide functionalized biomolecules (122), e.g., an oligonucleotide, can be conjugated with thio on (121).

Example 6

"Direct" Synthesis Scheme for a Branched Linking Molecule

Figure 19:
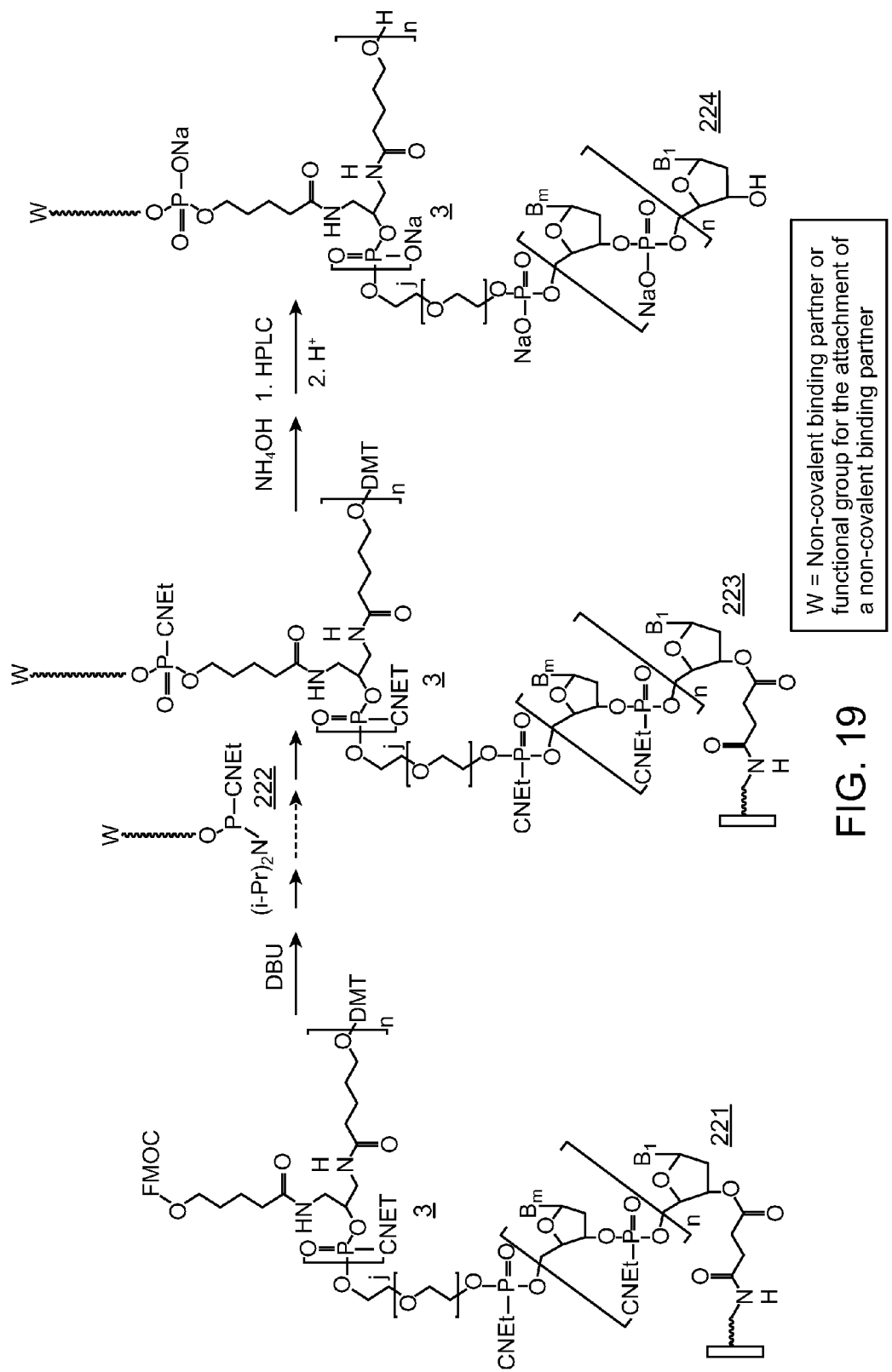
FIG. 19 illustrates a scheme for the direct synthesis of a branched linking molecule comprising an ODN target specific binding moiety and multiple first members of a non-covalent binding pair.

Another approach, described in FIG. 19, is to synthesize and modify a branched linker at the 5'-terminal of an oligonucleotide on solid phase. Many functional groups and molecules can be linked on the side chains of the branched linker.

An oligonucleotide can be synthesized on a solid support using phosphoramidite synthesis chemistry. Optionally, a chemical spacer can be incorporated on the terminal of the oligonucleotide with spacers bearing phosphoramidite. Then, a branched entity can be synthesized directly onto the oligonucleotide or on the spacer, if present. After removing the DMT protecting group from the oligonucleotide or the spacer, a unit of "Y" shape bifunctional monomer (2) is coupled to the exposed hydroxyl group using phosphoramidite synthesis chemistry. The "Y" shape bifunctional monomer (2) has two different protecting groups at each terminal: DMT, an acid labile group, and FMOC, a base labile group. The DMT group is deblocked using acidic solution, and then another unit of the "Y" shape bifunctional monomer (2) is incorporated to extend the branch backbone. By repeating this process a pre-determined number of the "Y" shape bifunctional monomer (2) can be incorporated to form (221) with branched structure.

The FMOC protecting groups on the side chains of the branched entity can be removed using a weak base solution, e.g., DBU in acetonitrile, to expose the hydroxyl groups which can be modified to form many functional groups or conjugate with biomolecules. These modifications can be introduced using suitable phosphoramidite modifiers (222). Functional groups and molecules used in the modification can include, e.g., alkyne, azide, biotin, amine, carboxy, hydrazide, aldehyde, oligonucleotide, etc.

The synthesized oligonucleotide and branched linker (223) bearing multiple functional groups or molecules on the side chains is deprotected and cleaved from the solid support by concentrated ammonium hydroxide. The ammonia is removed by evaporation. The desired branched linker product containing a trityl hydrophobic group is isolated from the crude mixture using HPLC. The trityl group is cleaved by treating with acid and can be removed by n-butanol extraction. The pure oligonucleotide and branched linker (224) bearing multiple functional groups or molecules on the side chains can be utilized for many applications, including but not limited to the cross-linking of a nucleic acid target molecule and a magnetic particle on a MTJ biosensor.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of generating a complex comprising a nucleic acid target molecule, said method comprising:
 combining in a reaction mixture
  a substrate surface, wherein said substrate surface comprises at least one target-immobilization probe bound thereto;
  a detectable particle having a diameter of from 0.2 µm to 5 µm, wherein said detectable particle comprises a plurality of capture probes bound thereto;
  a sample suspected of containing a nucleic acid target molecule; and
  a linking molecule, wherein said linking molecule comprises
   a plurality of non-continuous target-specific binding sequences which specifically bind to said nucleic acid target molecule, when present, wherein each of said non-continuous target-specific binding sequences specifically binds to a different region of said nucleic acid target molecule when present, and
   a plurality of non-continuous capture probe-specific binding sequences, wherein each of said non-continuous capture probe-specific binding sequences specifically binds to one of said plurality of capture probes,
 wherein said combining is under reaction conditions sufficient to provide for specific binding of said nucleic acid target molecule, if present, to said target-immobilization probe, and
 wherein said combining is under reaction conditions sufficient to provide for specific binding of said linking molecule to said nucleic acid target molecule, if present, and to a plurality of said capture probes,
 wherein, when said nucleic acid target molecule is present in said sample, said target-immobilization probe specifically binds to said nucleic acid target molecule, said nucleic acid target molecule specifically binds to said linking molecule, and said linking molecule specifically binds to a plurality of the capture probes bound to the detectable particle, thereby forming a complex comprising said substrate surface, said target immobilization probe, said nucleic acid target molecule, said linking molecule and said detectable particle, and wherein said complex does not comprise more than one of said detectable particle.

2. The method of claim 1, further comprising adding to the reaction mixture a cross-linking agent to form covalent bonds between specifically bound nucleic acid molecules, if present.

3. The method of claim 1, wherein the linking molecule has a branched structure.

4. The method of claim 1, wherein the linking molecule has a linear structure.

5. The method of claim 1, wherein the plurality of non-contiguous target-specific binding sequences are covalently linked to the plurality of non-contiguous capture probe-specific binding sequences in the linking molecule.

6. A reaction mixture comprising:
a substrate surface, wherein said substrate surface comprises at least one target-immobilization probe bound thereto;
a detectable particle having a diameter of from 0.2 μm to 5 μm, wherein said detectable particle comprises a plurality of capture probes bound thereto;
a sample suspected of containing a nucleic acid target molecule; and
a linking molecule, wherein said linking molecule comprises
a plurality of non-contiguous target-specific binding sequences which specifically bind to said nucleic acid target molecule, when present, wherein each of said non-contiguous target-specific binding sequences specifically binds to a different region of said nucleic acid target molecule when present, and
a plurality of non-contiguous capture probe-specific binding sequences, wherein each of said non-contiguous capture probe-specific binding sequences specifically binds to one of said plurality of capture probes,
wherein, when said nucleic acid target molecule is present in said sample, said target-immobilization probe specifically binds to said nucleic acid target molecule, said nucleic acid target molecule specifically binds to said linking molecule, and said linking molecule specifically binds to a plurality of the capture probes bound to the detectable particle, thereby forming a complex comprising said substrate surface, said target immobilization probe, said nucleic acid target molecule, said linking molecule and said detectable particle, and
wherein said complex does not comprise more than one of said detectable particle.

7. The reaction mixture of claim 6, wherein said detectable particle is a magnetic particle.

8. The reaction mixture of claim 6, wherein the linking molecule has a branched structure.

9. The reaction mixture of claim 6, wherein the linking molecule has a linear structure.

10. The reaction mixture of claim 6, wherein the plurality of non-contiguous target-specific binding sequences are covalently linked to the plurality of non-contiguous capture probe-specific binding sequences in the linking molecule.

11. A method of generating a complex comprising a nucleic acid target molecule, said method comprising:
combining in a reaction mixture
a substrate surface, wherein said substrate surface comprises at least one target-immobilization probe bound thereto;
a detectable particle having a diameter of from 0.2 μm to 5 μm, wherein said detectable particle comprises a plurality of capture probes bound thereto;
a sample suspected of containing a nucleic acid target molecule; and
a plurality of linking molecules, wherein each member of said plurality of linking molecules is independently present in one or more copies, and wherein each member comprises
a target-specific binding sequence which specifically binds to a different region of said nucleic acid target molecule, when present, and
a capture probe-specific binding sequence which specifically binds to a capture probe of said plurality of capture probes,
wherein said combining is under reaction conditions sufficient to provide for specific binding of said nucleic acid target molecule, if present, to said target-immobilization probe, and
wherein said combining is under reaction conditions sufficient to provide for specific binding of said plurality of linking molecules to said nucleic acid target molecule, if present, and to a plurality of the capture probes bound to the detectable particle,
wherein, when said nucleic acid target molecule is present in said sample, said target-immobilization probe specifically binds to said nucleic acid target molecule, and said plurality of linking molecules specifically binds to a plurality of different regions of said nucleic acid target molecule and a plurality of the capture probes bound to the detectable particle, thereby forming a complex comprising said substrate surface, said target immobilization probe, said nucleic acid target molecule, said plurality of linking molecules, and said detectable particle, and
wherein said complex does not comprise more than one of said detectable particle.

12. The method of claim 11, further comprising adding to the reaction mixture a cross-linking agent to form covalent bonds between specifically bound nucleic acid molecules, if present.

13. The method of claim 11, wherein the target-specific binding sequence and the capture probe-specific binding sequence are covalently linked in each member of the plurality of linking molecules.

14. A reaction mixture comprising:
a substrate surface, wherein said substrate surface comprises at least one target-immobilization probe bound thereto;
a detectable particle having a diameter of from 0.2 μm to 5 μm, wherein said detectable particle comprises a plurality of capture probes bound thereto;
a sample suspected of containing a nucleic acid target molecule; and
a plurality of linking molecules, wherein each member of said plurality of linking molecules is independently present in one or more copies, and wherein each member comprises
a target-specific binding sequence which specifically binds to a different region of said nucleic acid target molecule, when present; and
a capture probe-specific binding sequence which specifically binds to a capture probe of said plurality of capture probes,
wherein when said nucleic acid target molecule is present in said sample, said target-immobilization probe specifically binds to said nucleic acid target molecule, and said plurality of linking molecules specifically binds to a plurality of different regions of said nucleic acid target molecule and a plurality of the capture probes bound to the detectable particle, thereby forming a complex comprising said substrate surface, said target immobilization probe, said nucleic acid target molecule, said plurality of linking molecules, and said detectable particle, and wherein said complex does not comprise more than one of said detectable particle.

15. The reaction mixture of claim 14, wherein said detectable particle is a magnetic particle.

16. The reaction mixture of claim 14, wherein the target-specific binding sequence and the capture probe-specific binding sequence are covalently linked in each member of the plurality of linking molecules.

17. A method of generating a complex comprising a nucleic acid target molecule, said method comprising:
combining in a reaction mixture
a substrate surface, wherein said substrate surface comprises a plurality of capture probes bound thereto;
a detectable particle having a diameter of from 0.2 μm to 5 μm, wherein said detectable particle comprises a plurality of capture probes bound thereto;
a sample suspected of containing a nucleic acid target molecule;
a first linking molecule, wherein said first linking molecule comprises
a plurality of non-continuous target-specific binding sequences which specifically bind to said nucleic acid target molecule, when present, wherein each of said non-continuous target-specific binding sequences specifically binds to a different region of said nucleic acid target molecule when present, and
a plurality of non-continuous capture probe-specific binding sequences, wherein each of said non-continuous capture probe-specific binding sequences specifically binds to one of the plurality of capture probes bound to the detectable particle;
and
a second linking molecule, wherein said second linking molecule comprises
a plurality of non-continuous target-specific binding sequences which specifically bind to said nucleic acid target molecule, when present, wherein each of said non-continuous target-specific binding sequences specifically binds to a different region of said nucleic acid target molecule when present, and
a plurality of non-continuous capture probe-specific binding sequences, wherein each of said non-continuous capture probe-specific binding sequences specifically binds to one of the plurality of capture probes bound to the substrate surface,
wherein said combining is under reaction conditions sufficient to provide for specific binding of said first linking molecule to said nucleic acid target molecule, if present, and to a plurality of said capture probes bound to the detectable particle, and
wherein said combining is under reaction conditions sufficient to provide for specific binding of said second linking molecule to said nucleic acid target molecule, if present, and to a plurality of said capture probes bound to the substrate surface, and
wherein, when said nucleic acid target molecule is present in said sample, said first linking molecule specifically binds to said nucleic acid target molecule and a plurality the capture probes bound to the detectable particle, and said second linking molecule specifically binds to said nucleic acid target molecule and a plurality of the capture probes bound to the substrate surface, thereby forming a complex comprising said detectable particle, said first linking molecule, said nucleic acid target molecule, said second linking molecule and said substrate surface, and wherein said complex does not comprise more than one of said detectable particle.

18. The method of claim 17, further comprising adding to the reaction mixture a cross-linking agent to form covalent bonds between specifically bound nucleic acid molecules, if present.

19. The method of claim 17, wherein the first linking molecule and/or the second linking molecule has a branched structure.

20. The method of claim 17, wherein the first linking molecule and/or the second linking molecule has a linear structure.

21. The method of claim 17, wherein the plurality of non-contiguous target-specific binding sequences of the first linking molecule are covalently linked to the plurality of non-contiguous capture probe-specific binding sequences of the first linking molecule, and wherein the plurality of non-contiguous target-specific binding sequences of the second linking molecule are covalently linked to the plurality of non-contiguous capture probe-specific binding sequences of the second linking molecule.

22. A reaction mixture comprising:
a substrate surface, wherein said substrate surface comprises a plurality of capture probes bound thereto;
a detectable particle having a diameter of from 0.2 μm to 5 μm, wherein said detectable particle comprises a plurality of capture probes bound thereto;
a sample suspected of containing a nucleic acid target molecule;
a first linking molecule, wherein said first linking molecule comprises
a plurality of non-continuous target-specific binding sequences which specifically bind to said nucleic acid target molecule, when present, wherein each of said non-contiguous target-specific binding sequences specifically binds to a different region of said nucleic acid target molecule when present, and
a plurality of non-contiguous capture probe-specific binding sequences, wherein each of said non-contiguous capture probe-specific binding sequences specifically binds to one of the plurality of capture probes bound to the detectable particle;
and
a second linking molecule, wherein said second linking molecule comprises
a plurality of non-contiguous target-specific binding sequences which specifically bind to said nucleic acid target molecule, when present, wherein each of said non-contiguous target-specific binding sequences specifically binds to a different region of said nucleic acid target molecule when present, and
a plurality of non-contiguous capture probe-specific binding sequences wherein each of said non-contiguous capture probe-specific binding sequences specifically binds to one of the plurality of capture probes bound to the substrate surface,
wherein, when said nucleic acid target molecule is present in said sample, said first linking molecule specifically binds to said nucleic acid target molecule and a plurality of the capture probes bound to the detectable particle, and said second linking molecule specifically binds to said nucleic acid target molecule and a plurality of the capture probes bound to the substrate surface, thereby forming a complex comprising said detectable particle, said first linking molecule, said nucleic acid target molecule, said second linking molecule and said substrate surface, and wherein said complex does not comprise more than one of said detectable particle.

23. The reaction mixture of claim 22, wherein said detectable particle is a magnetic particle.

24. The reaction mixture of claim 22, wherein the first linking molecule and/or the second linking molecule has a branched structure.

25. The reaction mixture of claim 22, wherein the first linking molecule and/or the second linking molecule has a linear structure.

26. The reaction mixture of claim 22, wherein the plurality of non-contiguous target-specific binding sequences of the first linking molecule are covalently linked to the plurality of non-contiguous capture probe-specific binding sequences of the first linking molecule, and wherein the plurality of non-contiguous target-specific binding sequences of the second linking molecule are covalently linked to the plurality of non-contiguous capture probe-specific binding sequences of the second linking molecule.

27. A method of generating a complex comprising a nucleic acid target molecule, said method comprising:
combining in a reaction mixture
a substrate surface, wherein said substrate surface comprises a plurality of capture probes bound thereto;
a detectable particle having a diameter of from 0.2 μm to 5 μm, wherein said detectable particle comprises a plurality of capture probe bound thereto;
a sample suspected of containing a nucleic acid target molecule;
a first plurality of linking molecules, wherein each member of said first plurality of linking molecules is independently present in one or more copies, and wherein each member comprises
a target-specific binding sequence which specifically binds to a different region of said nucleic acid target molecule, when present, and
a capture probe-specific binding sequence which specifically binds to a capture probe of said plurality of capture probes bound to the detectable particle; and
a second plurality of linking molecules, wherein each member of said second plurality of linking molecules is independently present in one or more copies, and wherein each member comprises
a target-specific binding sequence which specifically binds to a different region of said nucleic acid target molecule, when present, and
a capture probe-specific binding sequence which specifically binds to a capture probe of said plurality of capture probes bound to the substrate surface,
wherein said combining is under reaction conditions sufficient to provide for specific binding of said first plurality of linking molecules to said nucleic acid target molecule, if present, and to a plurality of the capture probes bound to the detectable particle, and
wherein said combining is under reaction conditions sufficient to provide for specific binding of said second plurality of linking molecules to said nucleic acid target molecule, if present, and to a plurality of the capture probes bound to the substrate surface, and
wherein, when said nucleic acid target molecule is present in said sample, said first plurality of linking molecules specifically binds to a plurality of different regions of said nucleic acid target molecule and a plurality of the capture probes bound to the detectable particle, and said second plurality of linking molecules specifically binds to a plurality of different regions of said nucleic acid target molecule and a plurality of the capture probes bound to the substrate surface, thereby forming a complex comprising said detectable particle, said first plurality of linking molecules, said nucleic acid target molecule, said second plurality of linking molecules and said substrate surface, and wherein said complex does not comprise more than one of said detectable particle.

28. The method of claim 27, further comprising adding to the reaction mixture a cross-linking agent to form covalent bonds between specifically bound nucleic acid molecules, if present.

29. The method of claim 27, wherein the target-specific binding sequence and the capture probe-specific binding sequence for each member of the first plurality of linking molecules are covalently linked in each member of the first plurality of linking molecules, and wherein the target-specific binding sequence and the capture probe-specific binding sequence for each member of the second plurality of linking molecules are covalently linked in each member of the second plurality of linking molecules.

30. A reaction mixture comprising:
a substrate surface, wherein said substrate surface comprises a plurality of capture probes bound thereto;
a detectable particle having a diameter of from 0.2 μm to 5 μm, wherein said detectable particle comprises a plurality of capture probes bound thereto;
a sample suspected of containing a nucleic acid target molecule;
a first plurality of linking molecules, wherein each member of said first plurality of linking molecules is independently present in one or more copies, and wherein each member comprises
a target-specific binding sequence which specifically binds to a different region of said nucleic acid target molecule, when present, and
a capture probe-specific binding sequence which specifically binds to a capture probe of said plurality of capture probes bound to the detectable particle; and
a second plurality of linking molecules, wherein each member of said second plurality of linking molecules is independently present in one or more copies, and wherein each member comprises
a target-specific binding sequence which specifically binds to a different region of said nucleic acid target molecule, when present, and
a capture probe-specific binding sequence which specifically binds to a capture probe of said plurality of capture probes bound to the substrate surface,
wherein, when said nucleic acid target molecule is present in said sample, said first plurality of linking molecules specifically binds to a plurality of different regions of said nucleic acid target molecule and a plurality of the capture probes bound to the detectable particle, and said second plurality of linking molecules specifically binds to a plurality of different regions of said nucleic acid target molecule and a plurality of the capture probes bound to the substrate surface, thereby forming a complex comprising said detectable particle, said first plurality of linking molecules, said nucleic acid target molecule, said second plurality of linking molecules and said substrate surface, and wherein said complex does not comprise more than one of said detectable particle.

31. The reaction mixture of claim 30, wherein said detectable particle is a magnetic particle.

32. The reaction mixture of claim 30, wherein the target-specific binding sequence and the capture probe-specific binding sequence for each member of the first plurality of linking molecules are covalently linked in each member of the first plurality of linking molecules, and wherein the target-specific binding sequence and the capture probe-specific binding sequence for each member of the second plurality of linking molecules are covalently linked in each member of the second plurality of linking molecules.

* * * * *

UNITED STATES PATENT AND TRADEMARK OFFICE
CERTIFICATE OF CORRECTION

PATENT NO. : 9,150,910 B2
APPLICATION NO. : 12/612203
DATED : October 6, 2015
INVENTOR(S) : Celine Hu et al.

Page 1 of 1

It is certified that error appears in the above-identified patent and that said Letters Patent is hereby corrected as shown below:

In the Claims

Column 34, line 39, please replace "non-continuous" with --non-contiguous--
Column 34, line 42, please replace "non-continuous" with --non-contiguous--
Column 34, line 45, please replace "non-continuous" with --non-contiguous--
Column 34, line 46, please replace "non-continuous" with --non-contiguous--

Column 37, line 25, please replace "non-continuous" with --non-contiguous--
Column 37, line 28, please replace "non-continuous" with --non-contiguous--
Column 37, line 31, please replace "non-continuous" with --non-contiguous--
Column 37, line 32, please replace "non-continuous" with --non-contiguous--
Column 37, line 39, please replace "non-continuous" with --non-contiguous--
Column 37, line 42, please replace "non-continuous" with --non-contiguous--
Column 37, line 45, please replace "non-continuous" with --non-contiguous--
Column 37, line 46, please replace "non-continuous" with --non-contiguous--

Column 38, line 35, please replace "non-continuous" with --non-contiguous--

Signed and Sealed this
Fifth Day of July, 2016

Michelle K. Lee
*Director of the United States Patent and Trademark Office*